US008388966B2

(12) United States Patent
Gevas et al.

(10) Patent No.: US 8,388,966 B2
(45) Date of Patent: Mar. 5, 2013

(54) COMBINATION TREATMENT OF PANCREATIC CANCER

(75) Inventors: Philip C. Gevas, Key Biscayne, FL (US); Dov Michaeli, Larkspur, CA (US); Stephen Grimes, Davis, CA (US); Martyn Caplin, London (GB)

(73) Assignee: Cancer Advances, Inc., Durham, NC (US)

( * ) Notice: Subject to any disclaimer, the term of this patent is extended or adjusted under 35 U.S.C. 154(b) by 18 days.

(21) Appl. No.: 12/221,956

(22) Filed: Aug. 8, 2008

(65) Prior Publication Data
US 2009/0004200 A1 Jan. 1, 2009

Related U.S. Application Data

(63) Continuation of application No. 11/360,378, filed on Feb. 22, 2006, now abandoned, which is a continuation of application No. 10/104,607, filed on Mar. 22, 2002, now abandoned.

(60) Provisional application No. 60/278,294, filed on Mar. 23, 2001.

(51) Int. Cl.
*A61K 39/00* (2006.01)
*A61K 39/395* (2006.01)

(52) U.S. Cl. ............... 424/139.1; 424/141.1; 424/143.1; 424/185.1

(58) Field of Classification Search .................. None
See application file for complete search history.

(56) References Cited

U.S. PATENT DOCUMENTS

| | | | |
|---|---|---|---|
| 3,931,141 A | 1/1976 | Wissmann | |
| 4,069,313 A | 1/1978 | Woodhour et al. | |
| 4,196,265 A | 4/1980 | Koprowski et al. | |
| 4,201,770 A | 5/1980 | Stevens | 424/185.1 |
| 4,302,386 A | 11/1981 | Stevens | 260/112.5 |
| 4,384,995 A | 5/1983 | Stevens | 260/112.5 |
| 4,526,716 A | 7/1985 | Stevens | 260/112.5 |
| 4,565,805 A | 1/1986 | Smirnov | |
| 4,687,759 A | 8/1987 | Martinez et al. | |
| 4,691,006 A | 9/1987 | Stevens | 530/324 |
| 4,713,366 A | 12/1987 | Stevens | 514/13 |
| 4,762,913 A | 8/1988 | Stevens | |
| 4,767,842 A | 8/1988 | Stevens | 530/324 |
| 4,794,103 A | 12/1988 | Bertolini | |
| 4,803,170 A | 2/1989 | Stanton et al. | |
| 4,816,567 A | 3/1989 | Cabilly et al. | |
| 4,840,939 A | 6/1989 | Leveen et al. | |
| 4,894,443 A | 1/1990 | Greenfield et al. | |
| 4,923,819 A | 5/1990 | Fernandez et al. | |
| 4,925,922 A | 5/1990 | Byers et al. | |
| 4,971,792 A | 11/1990 | Steplewski et al. | |
| 4,978,683 A | 12/1990 | Rovati et al. | |
| 4,997,950 A | 3/1991 | Murphy et al. | |
| 5,006,334 A | 4/1991 | Stevens | |
| 5,023,077 A | 6/1991 | Gevas et al. | 424/185.1 |
| 5,035,988 A | 7/1991 | Nakamura et al. | |
| 5,055,404 A | 10/1991 | Ueda et al. | |
| 5,110,911 A | 5/1992 | Samuel et al. | |
| 5,120,829 A | 6/1992 | Pierschbacher et al. | |
| 5,162,504 A | 11/1992 | Horoszewicz | |
| 5,164,299 A | 11/1992 | Lambert | |
| 5,242,799 A | 9/1993 | Samuel et al. | |
| 5,256,542 A | 10/1993 | Chang | |
| 5,319,073 A | 6/1994 | Wank | |
| 5,468,494 A * | 11/1995 | Gevas et al. | 424/195.11 |
| 5,484,596 A | 1/1996 | Hanna, Jr. et al. | |
| 5,580,563 A | 12/1996 | Tam et al. | |
| 5,585,474 A | 12/1996 | Iwaki et al. | |
| 5,607,676 A | 3/1997 | Gevas et al. | 424/197.11 |
| 5,609,870 A | 3/1997 | Gevas et al. | 424/184.1 |
| 5,622,702 A | 4/1997 | Gevas et al. | 424/184.1 |
| 5,639,613 A | 6/1997 | Shay et al. | |
| 5,643,735 A | 7/1997 | Yokoi et al. | 435/7.9 |
| 5,665,864 A | 9/1997 | Quaranta et al. | |
| 5,665,874 A | 9/1997 | Kuhajda et al. | |
| 5,668,117 A | 9/1997 | Shapiro | |
| 5,683,695 A | 11/1997 | Shen et al. | |
| 5,688,504 A | 11/1997 | Morgan, Jr. | |
| 5,688,506 A | 11/1997 | Grimes et al. | 424/184.1 |
| 5,698,201 A | 12/1997 | Stevens | |
| 5,703,213 A | 12/1997 | Wands et al. | |
| 5,712,369 A | 1/1998 | Old et al. | |
| 5,723,718 A | 3/1998 | Berens | |
| 5,731,159 A | 3/1998 | Waldman | |
| 5,733,790 A | 3/1998 | Potter et al. | |
| 5,736,146 A | 4/1998 | Cohen et al. | |
| 5,750,119 A | 5/1998 | Srivastava | |
| 5,759,551 A | 6/1998 | Ladd et al. | |
| 5,759,791 A | 6/1998 | Kuhajda et al. | |
| 5,767,242 A | 6/1998 | Zimmermann et al. | |
| 5,770,576 A | 6/1998 | Morozov et al. | |
| 5,785,970 A | 7/1998 | Gevas et al. | 424/184.1 |
| 5,786,213 A | 7/1998 | Singh et al. | |

(Continued)

FOREIGN PATENT DOCUMENTS

| | | |
|---|---|---|
| EP | 380230 | 11/1994 |
| EP | 755683 | 1/1997 |

(Continued)

OTHER PUBLICATIONS

Smith et al (Am J Physiology, 1996, vol. 5, pt. 2, pp. 1078-1084).*
abstract of Taetle et al (JNCI, 1994, vol. 86, pp. 450-455).*
Rodriguez-Lescure et al (Proceeding of the Annual Meeting of the American Society of Clinical Oncology, 1999, vol. 18, abstract 1143).*
Bruns et al (Cancer Research, 2000, vol. 60, pp. 2-7).*
"ADAP drugs: leucovorin," Access Project, http://www.aegis.com/factshts/network/access/drugs/leuc.html (1996) (accessed on Aug. 13, 2004), 1 page.
"*Prilosec* OTC Review: Two Advisory Committee Members Weigh in Without Voting," The Pink Sheet. pp. 22-23 (2002).

(Continued)

*Primary Examiner* — Karen Canella
(74) *Attorney, Agent, or Firm* — Jenkins, Wilson, Taylor & Hunt, P.A.

(57) ABSTRACT

A combination for use in the treatment of pancreatic cancer comprising:
  (i) an anti-gastrin effective immunogenic composition; and,
  (ii) one or more chemotherapeutic agents suitable for inhibiting cancer growth.

15 Claims, No Drawings

U.S. PATENT DOCUMENTS

| | | | |
|---|---|---|---|
| 5,788,964 A | 8/1998 | Baral et al. | |
| 5,827,691 A | 10/1998 | Iwaki et al. | |
| 5,843,446 A | 12/1998 | Ladd et al. | 424/181.1 |
| 5,866,128 A | 2/1999 | Gevas et al. | 424/184.1 |
| 5,866,617 A | 2/1999 | Hausheer et al. | |
| 5,869,045 A | 2/1999 | Hellstrom et al. | 424/130.1 |
| 5,879,898 A | 3/1999 | Tarin et al. | |
| 5,932,412 A | 8/1999 | Dillner et al. | |
| 5,955,504 A | 9/1999 | Wechter et al. | |
| 5,981,167 A | 11/1999 | Taremi et al. | |
| 6,132,720 A | 10/2000 | Grimes et al. | |
| 6,169,173 B1 | 1/2001 | Wank | 536/23.5 |
| 6,180,370 B1 | 1/2001 | Queen et al. | |
| 6,187,536 B1 | 2/2001 | Weinberg et al. | |
| 6,191,290 B1 | 2/2001 | Safavy | 549/510 |
| 6,251,581 B1 | 6/2001 | Ullman et al. | |
| 6,303,123 B1 | 10/2001 | Grimes et al. | 424/184.1 |
| 6,320,022 B1 | 11/2001 | Cutitta et al. | |
| 6,359,114 B1 | 3/2002 | Grimes et al. | 530/344 |
| 6,391,299 B1 | 5/2002 | Blackburn et al. | |
| 6,444,207 B1 | 9/2002 | Schoemaker et al. | |
| 6,472,506 B1 | 10/2002 | Moreau et al. | |
| 6,548,066 B1 | 4/2003 | Michaeli et al. | 424/185.1 |
| 6,565,813 B1 | 5/2003 | Garyantes | |
| 6,613,530 B1 | 9/2003 | Wienhues et al. | |
| 6,627,196 B1 | 9/2003 | Baughman et al. | |
| 6,639,055 B1 | 10/2003 | Carter et al. | |
| 6,689,869 B2 | 2/2004 | Waldmann et al. | |
| 6,696,262 B2 | 2/2004 | Harkonen | |
| 6,699,974 B2 | 3/2004 | Ono et al. | |
| 6,780,969 B2 | 8/2004 | Wang | |
| 6,815,414 B2 | 11/2004 | Chowers et al. | |
| 6,835,543 B2 | 12/2004 | Saitoh et al. | |
| 6,861,510 B1 | 3/2005 | Gevas et al. | 530/388.1 |
| 6,872,543 B1 | 3/2005 | Sipponen et al. | |
| 7,074,761 B1 | 7/2006 | Hinuma et al. | |
| 7,192,582 B2 | 3/2007 | Hudson et al. | |
| RE39,586 E | 4/2007 | Dagan | |
| 7,235,376 B2 | 6/2007 | Grimes et al. | |
| 7,300,918 B2 | 11/2007 | Rath | |
| 7,438,907 B2 | 10/2008 | Schuurman et al. | |
| 7,662,926 B2 | 2/2010 | Chan et al. | |
| 7,964,371 B2 | 6/2011 | Grimes et al. | |
| 8,013,115 B1 | 9/2011 | Garric et al. | |
| 8,158,128 B2 | 4/2012 | Grimes | |
| 8,343,930 B2 | 1/2013 | Gevas et al. | |
| 2001/0020005 A1 | 9/2001 | Chowers et al. | |
| 2002/0058040 A1 | 5/2002 | Grimes et al. | 424/185.1 |
| 2002/0095041 A1 | 7/2002 | Grimes et al. | 530/412 |
| 2003/0021786 A1 | 1/2003 | Gevas et al. | 424/146.1 |
| 2003/0049698 A1 | 3/2003 | Wang | |
| 2003/0068326 A1 | 4/2003 | Gevas et al. | 424/185.1 |
| 2003/0082643 A1 | 5/2003 | Hudson et al. | |
| 2003/0086941 A1 | 5/2003 | Michaeli et al. | 424/185.1 |
| 2003/0091574 A1 | 5/2003 | Gevas et al. | 424/155.1 |
| 2003/0138860 A1 | 7/2003 | Robertson et al. | |
| 2003/0232399 A1 | 12/2003 | Robertson et al. | |
| 2004/0001842 A1 | 1/2004 | Michaeli et al. | 424/185.1 |
| 2004/0063164 A1 | 4/2004 | Lassalle | |
| 2004/0266682 A1 | 12/2004 | Cruz | |
| 2005/0014138 A1 | 1/2005 | Rath | |
| 2005/0025770 A1 | 2/2005 | Gevas et al. | 424/155.1 |
| 2005/0069966 A1 | 3/2005 | Grimes et al. | 435/7.92 |
| 2005/0169979 A1 | 8/2005 | Michaeli et al. | 424/184.1 |
| 2005/0187152 A1 | 8/2005 | Gevas et al. | 514/12 |
| 2006/0020119 A1 | 1/2006 | Grimes et al. | 530/388.24 |
| 2006/0039911 A1 | 2/2006 | Gevas et al. | 424/145.1 |
| 2006/0140962 A1 | 6/2006 | Gevas et al. | |
| 2007/0031511 A1 | 2/2007 | Baldwin et al. | |
| 2007/0065454 A1 | 3/2007 | Michaeli et al. | |
| 2007/0066809 A1 | 3/2007 | Grimes | |
| 2007/0082043 A1 | 4/2007 | Michaeli et al. | |
| 2007/0248608 A1 | 10/2007 | Grimes et al. | |
| 2007/0249005 A1 | 10/2007 | Grimes et al. | |
| 2009/0191232 A1 | 7/2009 | Gevas et al. | |
| 2010/0129382 A1 | 5/2010 | Gevas et al. | |
| 2011/0117108 A1 | 5/2011 | Gevas et al. | |

FOREIGN PATENT DOCUMENTS

| | | |
|---|---|---|
| EP | 0 818 680 | 1/1998 |
| EP | 1129724 | 9/2001 |
| EP | 1 579 863 | 9/2005 |
| JP | 06107564 A | 4/1994 |
| WO | WO 90/08774 | 8/1990 |
| WO | WO94/00590 | 1/1994 |
| WO | WO94/07530 | 4/1994 |
| WO | WO95/04544 | 2/1995 |
| WO | WO 95/13297 | 5/1995 |
| WO | WO95/21380 | 8/1995 |
| WO | WO96/15456 | 5/1996 |
| WO | WO97/28821 | 8/1997 |
| WO | WO97/38584 | 10/1997 |
| WO | WO98/31393 | 7/1998 |
| WO | WO98/51337 | * 11/1998 |
| WO | WO99/19353 | 4/1999 |
| WO | WO 99/59612 | 11/1999 |
| WO | WO 99/59628 | 11/1999 |
| WO | WO 99/59631 | 11/1999 |
| WO | WO99/65513 | 12/1999 |
| WO | WO00/67035 | 11/2000 |
| WO | WO01/13114 | 2/2001 |
| WO | WO 01/34192 | 5/2001 |
| WO | WO 01/77685 | 10/2001 |
| WO | WO02/39123 | 5/2002 |
| WO | WO02/076499 | 10/2002 |
| WO | WO03/005955 | 1/2003 |
| WO | WO2004/023148 | 3/2004 |
| WO | WO2004/088326 | 10/2004 |
| WO | WO2005/095459 | 10/2005 |
| WO | WO 2006/008649 | 1/2006 |
| WO | WO 2006/016275 | 2/2006 |
| WO | WO 2006/032980 | 3/2006 |
| WO | WO2007/062531 | 6/2007 |

OTHER PUBLICATIONS

Abdalla et al., "Gastrin-Induced Cyclooxygenase-2 Expression in Barrett's Carcinogenesis," Clinical Cancer Research. vol. 10 pp. 4784-4792 (2004).

Akai, "Co-existence and co-release of Gastrin 34 N-terminal Fragment with Gastrin 17 in Rat Stomach," Folla endocrinol, 64:1065-1080 (1988) [Abstract].

Asao et al., "Eradication of Hepatic Metastases of Carcinome H-59 by Combination Chemimmunotherapy with Liposomal Muramyl Tripeptide, 5-Fluorouracil, and Leucovorin," Cancer Research. vol. 52 pp. 6254-6257 (1992).

Baba et al., "Glycine-Extended Gastrin Induces Matrix Metalloproteinase-1- and -3-Mediated Invasion of Human Colon Cancer Cells Through Type 1 Collagen Gel and Matrigel," International Journal of Cancer. vol. 111, No. 1 pp. 23-31 (2004).

Baldwin et al., "Binding of the progastrin fragments to the 78 kDa gastrin-binding protein," FEBS Lett. vol. 359 pp. 97-100 (1995).

Baldwin, G.S., and Zhang, Q., "Measurement of Gastrin and Transforming Growth Factor α Messenger RNA Levels in Colonic Carcinoma Cell Lines by Quantitative Polymerase Chain Reaction," Cancer Research. vol. 52 pp. 2261-2267(1992).

Ballantyne, G.H., and Quin, J., "Surgical Treatment of Liver Metastasis in Patients with Colorectal Cancer," Cancer. vol. 71, No. 12 pp. 4252-4266 (1993).

Beacham et al., "Human Gastrin: Isolation, Structure and Synthesis: Synthesis of Human Gastrin I," Nature. vol. 209, No. 5023 pp. 585-586 (1966).

Beauchamp et al., "Proglumide, A Gastrin Receptor Antagonist, Inhibits Growth of Colon Cancer and Enhances Survival in Mice," Ann. Surg. vol. 202, No. 3 pp. 303-308 (1985).

Behr et al., "Cholecystokinin-B/Gastrin Receptor Binding Peptides: Preclinical Development and Evaluation of Their Diagnostic and Therapeutic Potential," Clinical Cancer Research. vol. 5 pp. 3124s-3138s (1999).

Beinborn et al., "A single amino acid of the cholecystokinin-B/gastrin receptor determines specificity for non-peptide antagonists," Nature. vol. 362 pp. 348-350 (1993).

Bentley et al., "Human Gastrin: Isolation, Structure and Synthesis," Nature. vol. 209, No. 5023 pp. 583-585 (1966).

Berg et al. in "Biochemistry," New York: W.H. Freeman and Co., 4.3.1-4.3.3 and Figure 4.35 (2002).
Bodey, "The significance of immunohistochemistry in the diagnosis and therapy of neoplasms," Expert Opin. Biol. Ther. vol. 2, No. 4 pp. 371-393 (2002).
Boland, "Editiorial: Gastrin and Colorectal Neoplasia—Chicken or Egg, or Both?" J. Clin. Gastroenterology. vol. 13, No. 5 pp. 497-499 (1991).
Bowie et al., "Deciphering the Message in Protein Sequences: Tolerance to Amino Acid Substitutions," Science. vol. 247 pp. 1306-1310 (1990).
Brett et al., "Lymphocyte Expression of the CCK-B/Gastrin Receptor (CCK-BR) in Gastric Lymphomas, Helicobacter pylori Gastritis and Normal Gastric Biopsies," Gastroenterology. vol. 114, No. 4, Suppl. 1 p. A570 (1998) [Abstract # G2333].
Brett et al., "The Effect of Antibodies Raised Against Gastrimmune on the Proliferation of Human Pancreatic Carcinoma Cell Lines," Gut. vol. 42 p. A26 (1998) [Abstract # W190].
Bystryn, J., "Tumor vaccines," Cancer and Metastasis Reviews. vol. 9 pp. 81-91 (1990).
Caplin et al., "Expression and Processing of Gastrin in Patients with Hepatocellular Carcinoma, Fibrolamellar Carcinoma and Cholangiocarcinoma," Gastroenterology. vol. 114, Suppl. I p. A1219 (1998) [Abstract # L0083].
Caplin et al., "Expression and Processing of Gastrin in Patients with Pancreatic Carcinoma," Gastroenterology. vol. 114, Suppl. 1 p. A445 (1998) [Abstract # G1809].
Caplin et al., "The CCK-B/Gastrin Receptor in Hepatocellular Carcinoma," Gastroenterology. vol. 110, No. 4 p. A1162 (1996) [Abstract].
Certificate of Patent corresponding to Japanese Patent Application No. 2006-509465 dated Feb. 25, 2011.
Certified English Translation of PCT Patent Application No. WO2001/13114, "Use of stabilized synthetic compounds in immunoassay." Publication date: Feb. 22, 2001.
Chaudhry et al., "Phase I and Imaging Trial of a Monoclonal Antibody Directed Against Gastrin-releasing Peptide in Patients with Lung Cancer," Clinical•Cancer Researc. vol. 5 pp. 3385-3393 (1999).
Choudhury et al., "N-Terminal Sequence of Human Big Gastrin: Sequence, Synthetic and Immunochemical Studies," A76 Hoppe-Seyler's Z. Physiol. Chem. vol. 361 pp. 1719-1733 (1980).
de Jong et al., "Effects of partial liver resection on tumor growth," Journal of Hepatology. vol. 25 pp. 109-121 (1996).
De Magistris, L., and Rehfeld, J.F., "A Simple Enzymatic Procedure for Radioimmunochemical Quantitation of the Large Molecular Forms of Gastrin and Cholecystokinin," Analytical Biochemistry. vol. 102 pp. 126-133 (1980).
Deed of Letters Patent corresponding to Australian Patent Application No. 2004225437 dated Aug. 26, 2010.
Dickinson, C.J., "Relationship of Gastrin Processing to Colon Cancer," Gastroenterology. vol. 109, No. 4 pp. 1384-1388 (1995).
Dockray, "Immunochemical Studies on Big Gastrin Using NH2-Terminal Specific Antisera," Regulatory Peptides. vol. 1 pp. 169-186 (1980).
Dockray, G.J., and Taylor, I.L., "Heptadecapeptide Gastrin: Measurement in Blood by Specific Radioimmunoassay", Gastroenterology. vol. 71, No. 6 pp. 971-977 (1976).
Dockray, G.J., and Walsh, J.H., "Amino-Terminal Gastrin Fragment in Serum of Zollinger-Ellison Syndrome Patients," Gastroenterology. vol. 68, No. 2 pp. 222-230 (1975).
Dockray et al., "Immunochemical studies on big gastrin using $NH_2$-terminal specific antiserums," Regulatory Peptides. vol. 1, No. 3 pp. 169-186 (1980). Chemical Abstracts vol. 94 pp. 506-507 (1981) [Abstract #94:119200w].
Dockray et al., "The Gastrins: Their Production and Biological Activities," Ann. Rv. Physiol. vol. 63 pp. 119-139 (2001).
Edgington, "Biotech Vaccines' Problematic Promise," Bio/Technology. vol. 10 pp. 763-766 (1992).
Edkins, J.S., "On the Chemical Mechanism of Gastric Secretion," Proceedings of the Royal Society of London. Series B, Containing Papers of a Biological Character. vol. 76, No. 510 p. 376 (1905).
Edkins, J.S., "The Chemical Mechanism of Gastric Secretion," J. Physiol. vol. 34, Nos. 1-2 pp. 133-144 (1906).

Erlichman et al., "A Randomized Trial of Fluorouracil and Colonic Acid in Patients With Metastatic Colorectal Carcinoma," Journal of Clinical Oncology. vol. 6 pp. 469-475 (1988).
Evans, "Chemotherapy in Advanced Non-Small Cell Lung Cancer," 37th Annual Meeting of the American Society of Clinical Oncology, Day 1, May 22, 2001, meeting report published by Medscape.
Fennerty, "Updated on Barrett's Esophagus" Digestive Diseases Week, May 22, 2001, meeting report published by Medscape, www.medscape.com, 6 pages.
Festen et al., "Effect of Oral Omeprazole on Serum Gastrin and Serum Pepsinogen I Levels," Gastroenterology. vol. 87, No. 5 pp. 1030-1034 (1984).
Feurle et al. "The Role of CCK and its Analogues in the Organogenesis of the Fetal Rat Pancreas," Pancreas. vol. 10, No. 3 pp. 281-286 (1995).
Fields, "Preparation of Antipeptide Antibodies: Introduction to Peptide Synthesis," Current Protocols in Molecular Biology. 11.15.1-11.15.9 (2002).
Fornai et al., "Cholecystokinin CCK2 receptors mediate the peptide's inhibitory actions on the contractile activity of human distal colon via the nitric oxide pathway," British Journal of Pharmacology. vol. 151 pp. 1246-1253 (2007).
Fraser, "Effects of Antibodies to Luteinizing Hormone Releasing Hormone on Reproductive Functions in Rodents," Immunization With Hormones in Reproduction Research. Nieschlag ed. North Holland Publishing. pp. 107-117 (1975).
Freston, "Long-Term Acid Control and Proton Pump Inhibitors: Interactions and Safety Issues in Perspective," American Journal of Gastroenterology. vol. 92, No. 4 pp. 51S-57S (1997).
Gil-Delgado et al., "Prospective Phase II Trial of Irinotecan, 5-Fluorouracil, and Leucovorin in Combinations as Salvage Therapy for Advanced Colorectal Cancer," American Journal of Clinical Oncology. vol. 24, No. 1 pp. 101-105 (2001).
Gilliam et al., "Randomized, double blind, placebo-controlled, multi-centre, group-sequential trial of G17DT for patients with advanced pancreatic cancer unsuitable or unwilling to take chemotherapy," Journal of Clinical Oncology. ASCO Annual Meeting Proceedings. vol. 22, No. 14S p. 2511 (2004) [Abstract].
Goetze, J.P., and Rehfeld, J.F., "Impact of Assay Epitope Specificity in Gastrinoma Diagnosis," Clinical Chemistry. vol. 49, No. 2 pp. 333-334 (2003).
Goletti et al. "Resection of Liver Gastrinoma Leading to Persistent Eugastrinemia," Eur. J. Surgery. vol. 158 pp. 55-57 (1992).
Grabowska, A., and Watson, S.A., "Downregulation of the Gastrin Gene Using Small Interfering RNA," Regulatory Peptides. vol. 122, No. 1 p. 46 (2004) [Abstract # A150].
Gregory, R.A., and Tracy, H.J., "Isolation of Two Gastrins from Human Antral Mucosa," Nature. vol. 209, No. 5023 p. 583 (1966).
Gutman et al., "Accelerated Growth of Human Colon Cancer Cells in Nude Mice Undergoing Liver Regeneration," Invasion and Metastasis. vol. 14, Nos. 1-6 pp. 362-371 (1994-1995).
Haigh et al. "Gastrin Induces Proliferation in Barrett's Metaplasia Through Activation of the CCK2 Receptor," Gastroenterology. vol. 124 pp. 615-625 (2003).
Hananel et al., "Hepatic Resection for Colorectal Liver Metastasis," The American Surgeon. vol. 61, No. 5 pp. 444-447 (1995).
Harlow, E., and Lane, D., Antibodies: A Laboratory Manual, Cold Spring Harbor Laboratory Press. Cold Spring Harbor, NY. pp. 7-13, 23-26, 142-143, 148-149 (1988).
Harlow, E., and Lane, D., Antibodies: A Laboratory Manual. Cold Spring Harbor Laboratory Press. Cold Spring Harbor, NY. pp. 555-556, 559, 561, 578-581, and 591-593 (1988).
Harris et al., "The Biological and Therapeutic Importance of Gastrin Gene Expression in Pancreatic Adenocarcinomas," Cancer Research. vol. 64 pp. 5624-5631 (2004).
Harrison et al. "The Effect of the Gastrin Receptor Antagonist Proglumide on Survival in Gastric Carcinoma," Cancer. vol. 66, No. 7 pp. 1449-1452 (1990).
He et al., "Biological Activity and Ferric Ion Binding of Fragments of Glycine-Extended Gastrin," Biochemistry. vol. 43, No. 37 pp. 11853-11861 (2004).

Henwood et al., "Expression of gastrin in developing gastric adenocarcinoma," British Journal of Surgery. vol. 88 pp. 564-568 (2001).

Houghten et al., "Relative Importance of Position and Individual Amino Acid Residues in Peptide Antigen-Antibody Interactions: Implications in the Mechanism of Antigenic Drift and Antigenic Shift," Vaccines. vol. 86 pp. 21-25 (1986).

Hughes et al., "Therapy with Gastrin Antibody in the Zollinger-Ellison Syndrome," Digestive Diseases. vol. 21 pp. 201-204 (1976).

Ichikawa et al., "Distinct effects of tetragastrin, histamine, and CCh on rat gastric mucin synthesis and contribution of NO," Am. J. Physiol. vol. 274, No. 1 pp. G138-G146 (1998).

Ikeda et al., "Preliminary report of tumor metastasis during liver regeneration after hepatic resection in rats," European Journal of Surgical Oncology. vol. 21, No. 2 pp. 188-190 (1995).

International Preliminary Examination Report corresponding to International Patent Application No. PCT/US2002/021768 dated Feb. 9, 2004.

International Preliminary Report on Patentability corresponding to International Patent Application No. PCT/US2005/010532 dated Nov. 3, 2006.

Issued Patent corresponding to Australian Patent Application No. 2005228897 dated Mar. 25, 2010.

Iwanaga et al., "Immunocytochemical Localization of the Different Gastrin Forms in the Pyloric Antrum," Biomedical Research. vol. 1 pp. 316-320 (1980).

Iwao et al., "Effects of Omeprazole and Lansoprazole on Fasting and Postprandial Serum Gastrin and Serum Pepsinogen A and C," Hepato-Gastroenterology. vol. 42 pp. 677-682 (1995).

Jaffe et al., "Gastrin resistance following immunization to the C-terminal tetrapeptide amide of gastrin," Surgery. vol. 69, No. 2 pp. 232-237 (1971).

Jaffe et al., "Inhibition of Endogenous Gastrin Activity by Antibodies to the Carboxyl-Terminal Tetrapeptide Amide of Gastrin," Gastroenterology. vol. 58, No. 2 pp. 151-156 (1970).

Jaffe et al., "Inhibition of gastrin activity by incubation with antibodies to the C-terminal tetrapeptide of gastrin," Surgery. vol. 65, No. 4 pp. 633-639 (1969).

Johnson, "New Aspects of the Trophic Action of Gastrointestinal Hormones," Gastroenterology. vol. 72, No. 4, Part 2 pp. 788-792 (1977).

Johnson et al, "Ornithine Decarboxylase in Large Bowel Mucosa: Regulation by Gastrin, Secretin and EGF," Journal of Physiology and Pharmacology. vol. 43, No. 1 pp. 33-41 (1992).

Joshi, S.N., and Gardner, J.D., "Gastrin and Colon Cancer: A Unifying Hypothesis," Digestive Diseases. vol. 14 pp. 334-344 (1996).

József et al., "A Gasztrin Aminoterminalis 1-13 Fragmensevel Kidolgozott,Szekvenciaspecifikus Radioimmunoassay," Izotoptechnika. vol. 25, No. 4 pp. 288-294 (1982) [Abstract].

Justin et al., "Gastric Acid Suppression Using Anti-Gastrin-17 Antibodies Produced by a Gastrin Immunogen, Gastrimmune, in an In Vivo Pig Model," Gastroenterology. vol. 108, No. 4 p. A125 (1995) [Abstract].

Kaiser, "First Pass at Cancer Genome Reveals Complex Landscape," Science. vol. 313 p. 1370 (2006).

Kameyama et al., "Adjuvant Chemo-Endocrine Chemotherapy with Gastrin Antagonist After Resection of Liver Metastasis in Colorectal Cancer," Japanese Journal of Cancer and Chemotherapy. vol. 21, No. 13 pp. 2169-2171 (1994) [Abstract].

Katoh et al., "Malignant Zollinger-Ellison Syndrome. Stabilizing of Liver Metastasis After Gastrectomy with Resection of Primary Tumor," The American Surgeon. vol. 56, No. 6 pp. 360-363 (1990).

Kelly et al., "pathophysiology of GI Tract and Liver: Expression of progastrin-derived peptides and gastrin receptors in a panel of gastrointestinal carcinoma cell lines," Journal of Gastroenterology and Hepatology. vol. 13 pp. 208-214 (1998).

Kipriyanov, S.M., and Little, M., "Generation of Recombinant Antibodies," Molecular Biotechnology. vol. 12 pp. 173-201 (1999).

Koelz, "Treatment of Reflux Esophagitis with H2-Blockers. Antacids and Prokinetic Drugs. An Analysis of Randomized Clinical Trials," Scandinavian Journal of Gastroenterology. Supplement 156 pp. 25-36 (1989).

Koh et al., "Gastrin Deficiency Results in Altered Gastric Differentiation and Decreased Colonic Proliferation in Mice," Gastroenterology. vol. 113, No. 3 pp. 1015-1025 (1997).

Koh et al., "Glycine-Extended Gastrin Promotes the Growth of Lung Cancer," Cancer Research. vol. 64 pp. 196-201 (2004).

Kothary, P.C., and Lvinik, A., "NH2-Terminal of Gastrin-17 in Duodenal Ulcer Disease: Identification of Progastrin-17," Biochemical and Biophysical Research Communications. vol. 146, No. 2 pp. 884-888 (1987).

Kovacs et al., "Gastrin Is a Major Mediator of the Gastric Phase of Acid Secretion in Dogs: Proof by Monoclonal Antibody Neutralization," Gastroenterology. vol. 97 pp. 1406-1413 (1989).

Kovacs et al. "Inhibition of sham feeding-stimulated acid secretion in dogs by immunoneutralization of gastrin," Am. J. Physiol. vol. 273 (Gastrointest. Liver Physiol. 36) pp. G399-403 (1997).

Kuipers et al., "The Efficacy and Safety of Long-term Omeprazole Treatment for Gastroesophageal Reflux Disease," Gastroenterology. vol. 118, No. 4 pp. 795-798 (2000).

Kusyk et al., "Stimulation of growth of a colon cancer cell line by gastrin," Am. J. Physiol. vol. 251 pp. G597-G601 (1986).

Lamberts et al., "Effects of Very Long (up to 10 years) Proton Pump Blockade on Human Gastric Mucosa," Digestion. vol. 64 pp. 205-213 (2001).

Lamers, C.B.H.W., and Jansen, J.B.M.J., "Role of Gastrin and Cholecystokinin in Tumours of the Gastrointestinal Tract," Eur. J. Cancer Clin. Oncol. vol. 24, No. 2 pp. 267-273 (1988).

Lamote, J., and Willems, G., "Stimulating effect of pentagastrin on cancer cell proliferation kinetics in chemically induced colon cancer in rats," Regulatory Peptides. vol. 20 pp. 1-9 (1988).

Larsson, "Histochemistry of gastrin Cells," Neurohistochemistry: Modern Methods and Applications. Alan R. Liss, Inc., pp. 527-567 (1986).

Larsson, L., and Rehfeld, J.F., "Characterization of Antral Gastrin Cells With Region-Specific Antisera," The Journal of Histochemistry and Cytochemistry. vol. 25, No. 12 pp. 1317-1321 (1977).

Laurie, S.A., and Kris, M.G. "Single-Agent Docetaxel (Taxotere) in the Treatment of Advanced Non-Small-Cell Lung Cancer: Clinical Concepts and Commentary," Clinical Lung Cancer. vol. 1, Suppl 1 pp. S5-S9 (2000).

Matsumoto et al. "Gastrin receptor characterization: affinity cross-linking of the gastrin receptor on canine gastric parietal cells," Am J. Physiol. vol. 252 p. G143-G147 (1987).

McCloy et al., "Pathophysiological Effects of Long-Term Acid Suppression in Man," Digestive Diseases and Sciences. vol. 40, No. 2 pp. 96S-120S [Supplement] (1995).

McGregor et al., "Trophic Effects of Gastrin on Colorectal Neoplasms in the Rat," Ann. Surg. vol. 195, No. 2 pp. 219-223 (1982).

Mizutani et al., "Promotion of hepatic metastases by liver resection in the rat," British J. Cancer. vol. 65, No. 6 pp. 794-797 (1992).

Moertel, C.G., "Chemotherapy for Colorectal Cancer," The New England Journal of Medicine. vol. 330, No. 16 pp. 1136-1142 (1994).

Moroder, L., and Wunsch, E., "Gastrins and Cholecystokinins: Chemical and Immunological Aspects," Gastrin and Cholecystokinin. Chemistry, physiology and pharmacology. (Ed. J. Bali et al.) Elsevier Science Publishers B.V. pp. 21-32 (1987).

Mu et al., "Monoclonal antibody to the gastrin receptor on parietal cells recognizes a 78-kDa protein," PNAS. vol. 84 pp. 2698-2702 (1987).

Nakata et al., "Cloning and Characterization of Gastrin Receptor From ECL Carcinoid Tumor of Mastomys Natalensis," Biochemical and Biophysical Research Communications. vol. 187, No. 2 pp. 1151-1157 (1992).

Narayan et al., "Characterization of gastrin binding to colonic mucosal membranes of guinea pigs," Molecular and Cellular Biochemistry. vol. 112 pp. 163-171 (1992).

NCBI Accession No. NP 795344 retrieved from http://www.ncbi.nlm.nih.gov on Dec. 12, 2007 (4 pages).

Nemeth et al., "Development of a sequence-specific radioimmunoassay by using N-terminal gastrin 1-13 antibody," Chemical Abstracts. vol. 98 p. 495 (1983) [Abstract # 98:51653].

Notice of Acceptance corresponding to Australian Patent Application No. 2004225437 dated Apr. 29, 2010.

Notice of Allowance corresponding to Japanese Patent Application No. 2006-509465 dated Jan. 18, 2011.
Notice of Allowance corresponding to U.S. Appl. No. 10/813,336 dated May 15, 2006.
Notice of Allowance corresponding to U.S. Appl. No. 10/813,336 dated Oct. 3, 2006.
Notice of Allowance corresponding to U.S. Appl. No. 10/813,336 dated Feb. 7, 2007.
Notice of Allowance corresponding to U.S. Appl. No. 11/800,889 dated Feb. 7, 2011.
Official Action corresponding to Canadian Patent Application No. 2,520,010 dated Nov. 1, 2010.
Official Action corresponding to Canadian Patent Application No. 2,561,405 dated Nov. 3, 2010.
Official Action corresponding to Canadian Patent Application No. 2,580,965 dated Sep. 30, 2010.
Official Action corresponding to Chinese Patent Application No. 200580036710.9 dated Feb. 24, 2011.
Official Action corresponding to European Patent Application No. 04 758 568.2-2404 dated Jul. 17, 2007.
Official Action corresponding to European Patent Application No. 05 730 336.4-1222 dated Apr. 27, 2007.
Official Action corresponding to Indian Patent Application No. 2441/CHENP/2005 dated Jul. 24, 2007.
Official Action corresponding to Indian Patent Application No. 6318/DELNP/2006/707 dated Jul. 5, 2010.
Official Action corresponding to Japanese Patent Application No. 2006-509465 dated Aug. 26, 2010.
Official Action corresponding to Japanese Patent Application No. 2007-506474 dated Jun. 1, 2010.
Official Action corresponding to U.S. Appl. No. 08/219,773 dated Oct. 19, 1994.
Official Action corresponding to U.S. Appl. No. 08/285,984 dated Feb. 7, 1995.
Official Action corresponding to U.S. Appl. No. 08/465,917 dated Aug. 12, 1996.
Official Action corresponding to U.S. Appl. No. 10/104,607 dated Mar. 29, 2005.
Official Action corresponding to U.S. Appl. No. 10/104,607 dated Nov. 21, 2005.
Official Action corresponding to U.S. Appl. No. 10/192,257 dated Sep. 21, 2005.
Official Action corresponding to U.S. Appl. No. 10/762,226 dated Dec. 27, 2006.
Official Action corresponding to U.S. Appl. No. 10/813,336 dated Jun. 23, 2005.
Official Action corresponding to U.S. Appl. No. 10/813,336 dated Oct. 20, 2005.
Official Action corresponding to U.S. Appl. No. 11/093,724 dated Nov. 25, 2005.
Official Action corresponding to U.S. Appl. No. 11/093,724 dated Feb. 6, 2006.
Official Action corresponding to U.S. Appl. No. 11/499,261 dated Mar. 15, 2007.
Official Action corresponding to U.S. Appl. No. 11/499,261 dated Nov. 30, 2007.
Official Action corresponding to U.S. Appl. No. 11/499,261 dated Sep. 24, 2008.
Official Action corresponding to U.S. Appl. No. 11/499,261 dated May 14, 2009.
Official Action corresponding to U.S. Appl. No. 11/499,621 dated Nov. 15, 2010.
Official Action corresponding to U.S. Appl. No. 11/663,126 dated Jun. 22, 2009.
Official Action corresponding to U.S. Appl. No. 11/663,126 dated Nov. 25, 2009.
Official Action corresponding to U.S. Appl. No. 11/663,126 dated Jun. 2, 2010.
Official Action corresponding to U.S. Appl. No. 11/800,889 dated Oct. 2, 2009.
Official Action corresponding to U.S. Appl. No. 11/800,889 dated Feb. 18, 2010.
Official Action corresponding to U.S. Appl. No. 11/800,889 dated Jun. 23, 2010.
Official Action corresponding to U.S. Appl. No. 12/693,127 dated Jul. 16, 2010.
Official Action corresponding to U.S. Appl. No. 12/693,127 dated Feb. 11, 2011.
Ohning et al., "Differential Kinetics for Immunoneutralization of Circulating Gastrin by Gastrin Monoclonal Antibody and Its $Fab_1$ Fragment in Rats," Peptides. vol. 15 pp. 417-423 (1994).
Ohsawa et al., "Effects of Three $H_2$-Receptor Antagonists (Cimetidine, Famotidine, Ranitidine) on Serum Gastrin Level," International Journal of Clinical Pharmacology Research. vol. 22, No. 2 pp. 29-35 (2002).
Palnæs Hansen et al., "Metabolism and Influence of Glycine-Extended Gastrin on Gastric Acid Secretion in Man," Digestion. vol. 57 pp. 22-29 (1996).
Pannequin et al., "Divergent roles for ferric ions in the biological activity of amidated and non-amidated gastrins," Journal of Endocrinology. vol. 181, No. 2 pp. 315-325 (2004).
Parsonnet et al., "Helicobacter Pylori Infection and the Risk of Gastric Carcinoma," The New England Journal of Medicine. vol. 325, No. 16 pp. 1127-1131 (1991).
Pauwels et al., "Identification of Progastrin in Gastrinomas, Antrum, and Duodenum by a Novel Radioimmunoassay," The Journal of Clinical Investigation. vol. 77 pp. 376-381 (1986).
Pawlikowski et al., "Gastrin and Somatostatin Levels in Patients with Gastric Cancer," Horm. Metabol. Res. vol. 21 pp. 89-91 (1989).
Petrelli et al., "The Modulation of Fluorouracil With Leucovorin in Metastatic Colorectal Carcinoma: A Prospective Randomized Phase III Trial," Journal of Clinical Oncology. vol. 7 pp. 1419-1426 (1989).
Petrioli et al., "Treatment of Advanced Colorectal Cancer with High-dose Intensity Folinic Acid and 5-Fluorouracil Plus Supportive Care," European Journal of Cancer. vol. 31A, No. 12 pp. 2105-2108 (1995).
Power et al. "A novel gastrin-processing pathway in mammalian antrum," Chemical Abstracts. vol. 109, No. 9 p. 113 (1988) [Abstract # 109:67341z].
Rae-Venter et al., "Gastrin Receptors in Human Colon Carcinoma," Gastroenterology. vol. 80, No. 5, Part 2 p. 1256 (1981) [Abstract].
Reddy, "Small Cell Lung Cancer: Improving Outcomes," American Society for Therapeutic Radiology and Oncology, 42nd Annual Meeting, Day 1, Oct. 22, 2000, meeting report published by Medscape.
Redmond, E.J., and Wetscher, G.J., "Gastroesophageal Reflux Disease," Ronald Hinder ed., R.G. Landes Company. pp. 1-6 (1993).
Rehfeld, "The New Biology of Gastrointestinal Hormones," Physiological Reviews. vol. 78, No. 4 pp. 1087-1108 (1998).
Rehfeld et al., "Production and Evaluation of Antibodies for the Radioimmunoassay of Gastrin," Scnad. J. Clin. Lab. Invest. vol. 30 pp. 221-232 (1972).
Rehfeld et al., "Sulfation of Gastrin: Effect on Immunoreactivity," Regulatory Peptides. vol. 2 pp. 333-342 (1981).
Ritter et al., "Serological Analysis of Human Anti-Human Antibody Responses in Colon Cancer Patients Treated with Repeated Doses of Humanized Monoclonal Antibody A33," Cancer Research. vol. 61 pp. 6851-6859 (2001).
Romani et al. "Gastrin Receptor Antagonist Ci-988 Inhibits Growth of Human Colon Cancer In Vivo and In Vitro," Aust. N.Z.J. Surgery. vol. 66 pp. 235-237 (1996).
Scheele et al., "Indicators of prognosis after hepatic resection for colorectal secondaries," Surgery. vol. 110, No. 1 pp. 13-29 (1991).
Scheithauer et al., "Combined Intraperitoneal plus Intravenous cChemotherapy after Curative Resection for Chronic Adenocarinome," European Journal of Cancer. vol. 31A, No. 12 pp. 1981-1986 (1995).
Schlom, "Monoclonal Antibodies: They're More and Less Than You Think," Molecular Foundations of Oncology. ed. Broder Williams & Williams, Baltimore MD, pp. 95-134 (1991).
Seitz et al., "Elevated Serum Gastrin Levels in Patients with Colorectal Neoplasia," J. Clin. Gastroenterol. vol. 13, No. 5 pp. 541-545 (1991).

Seva et al., "Characterization of the Glycine-Extended Gastrin (G-GLY) Receptor on AR4-2J Cells," Gastroenterology. vol. 108 p. A1005 (1995) [Abstract].

Seva et al., "Lorglumide and Loxglumide Inhibit Gastrin-stimulated DNA Synthesis in a Rat Tumoral Acinar Pancreatic Cell Line (AR42J)," Cancer Research. vol. 50, No. 8 pp. 5829-5833 (1990).

Siemann, "Satisfactory and Unsatisfactory Tumor Models: Factors Influencing the Selection of a Tumor Model for Experimental Evaluation," Rodent Tumor Models in Experimental Cancer Therapy (Ed. Kallman) Pergamon Press, NY. pp. 12-15 (1987).

Singh et al., "High Levels of Progastrin Significantly Increase Premalignant Changes in Colonic Mucosa of Mice in Tesponse to the Chemical Carcinogen, AOM," Gastroenterology. vol. 114, No. 4 p. A680 (1998) [Abstract # G2810].

Singh et al., "Novel Gastrin Receptors Mediate Mitogenic Effects of Gastrin and Processing Intermediates of Gastrin on Swiss 3T3 Fibroblasts. Absence of Detectable Cholecystokinin (CCK)-A and CCK-B Receptors," The Journal of Biological Chemistry. vol. 270, No. 15 pp. 8429-8438 (1995).

Singh et al., "Role of Gastrin and Gastrin Receptors on the Growth of a Transplantable Mouse Colon Carcinoma (MC-26) in BALB/c Mice," Cancer Research. vol. 46 pp. 1612-1616(1986).

Sipponen et al., "Serum Levels of Amidated Gastrin-17 and Pepsinogen I in Atrophic Gastritis: An Observational Case-Control Study," Scandinavian Journal of Gastroenterology. vol. 37, No. 7 pp. 785-791 (2002).

Slooter et al., "Tumor growth stimulation after partial hepatectomy can be reduced by treatment with tumor necrosis factor α," British Journal of Surgery. vol. 82 pp. 129-132 (1995).

Smith, J.P., and Solomon, T.E., "Effects of Gastrin, Proglumide, and Somatostatin on Growth of Human Colon Cancer," Gastroenterology. vol. 95, No. 6 pp. 1541-1548 (1988).

Smith et al., "Elevated Gastrin Levels in Patients with Colon Cancer or Adenomatous Polyps," Digestive Diseases and Science. vol. 34, No. 2 pp. 171-174 (1989).

Sobhani et al., "Chronic Endogenous Hypergastrinemia in Humans: Evidence for a Mitogenic Effect on the Colonic Mucosa," Gastroenterology. vol. 105, No. 1 pp. 22-30 (1993).

Sobhani et al., "Immunohistochemical characterization of gastrinomas with antibodies specific to different fragments of progastrin," Gastroentérologie Clinique et Biologique. vol. 13, No. 11 pp. 865-872 (1989).

Stepan et al., "Glycine-Extended Gastrin Exerts Growth-Promoting Effects on Human Colon Cancer Cells," Molecular Medicine. vol. 5, No. 3 pp. 147-159 (1999).

Sundler et al., "The Neuroendocrine System of the Gut—An Update," Acta Oncologica. vol. 30, No. 4 pp. 419-427 (1991).

Takhar et al., "The role of gastrin in colorectal carcinogenesis," J.R. Coll. Surg. Edinb. Irel. vol. 2, No. 5 pp. 251-257 (2004).

Talley et al., "Risk for Colorectal Adenocarcinoma in Pernicious Anemia," Annals of Internal Medicine. vol. 111, No. 9 pp. 738-742 (1989).

Taylor, "Chemotherapy, radiotherapy and immunotherapy of colorectal neoplasia," Current Opinion in Gastroenterology. vol. 9 pp. 28-33 (1993).

Tielemans et al., "Proliferation of Enterochromaffinlike Cells in Omeprazole-Treated Hypergastrinemic Rats," Gastroenterology. vol. 96, No. 3 pp. 723-729 (1989).

Trakal et al., "Diagnosis and Etiology of Barrett's Esophagus: Presence of Gastrin Secreting Cells," Acta Gastroenterológica Latinoamericana. vol. 15, No. 2 pp. 67-80 (1985) [Abstract].

UniProtKB/Swiss-Prot entry P01350, (1986) (accessed on Mar. 26, 2007).

Upp et al., "Polyamine Levels and Gastrin Receptors in Colon Cancers" Ann. Surg. vol. 207, No. 6 pp. 662-668 (1988).

Vaillant et al., "Cellular Origins of Different Forms of Gastrin. The Specific Immunocytochemical Localization of Related Peptides," The Journal of Histochemistry and Cytochemistry. vol. 27, No. 5 pp. 932-935 (1979).

Vaillant et al., "Repeat liver resection for recurrent colorectal metastasis," British J. Surgery. vol. 80, No. 3 pp. 340-344 (1993).

Varndell et al., "Intracellular topography of immunoreactive gastrin demonstrated using electron immunocytochemistry," Experienta. vol. 39 pp. 713-717 (1983).

Varro, A., and Dockray, G.J., "Post-translational processing of progastrin: inhibition of cleavage, phosphorylation and sulphation by brefeldin A," Biochem. J. vol. 295 pp. 813-819 (1993).

Varro, A., and Ardill, J.E.S., "Gastrin: an analytical review," Ann. Clin. Biochem. vol. 40 pp. 472-480 (2003).

Varro et al., "Pathways of Processing of the Gastrin Precursor in Rat Antral Mucosa," Journal of Clinical Investigation. vol. 95 pp. 1642-1649 (1995).

Varro et al., "The human gastrin precursor," Biochem. J. vol. 256 pp. 951-957 (1988).

Vauthey et al., "Factors Affecting Long-Term Outcome After Hepatic Resection for Hepatocellular Carcinoma," The American Journal of Surgery. vol. 169 pp. 28-35 (1995).

Von Hoff, D.D., and Bearss, D., "New drugs for patients with pancreatic cancer," Curr. Opin. Oncology. vol. 14 pp. 621-627 (2002).

Wang et al., "Processing and Proliferative Effects of Human Progastrin in Transgenic Mice," Journal of Clinical Investigation. vol. 98, No. 8 pp. 1918-1929 (1996).

Watson, S.A., and Steele, R.J.C., "Gastrin antagonists in the treatment of gastric cancer," Anti-Cancer Drugs. vol. 4, No. 6 pp. 599-604 (1993).

Watson et al., "Enhanced Inhibition of Pancreatic Cancer by Combination of the G17DT Immunogen and Gemcitabine," Amer. Soc. Clin. Oncol. vol. 37 (2002) [Abstract].

Watson et al., "Expression of CCKB/Gastrin Receptor Isoforms in Gastro-intestinal Tumour Cells," Int. J. Cancer. vol. 77, No. 4 pp. 572-577 (1998).

Watson et al., "Gastrin: growth enhancing effects on human gastric and colonic tumour cells," British Journal of Surgery. vol. 75, No. 4 pp. 554-558 (1988).

Watson et al., "Gastrin Inhibition Increases the Potency of Cytotoxic Agents in Pancreatic Cancer," Gastroenterology. vol. 122, No. 4 p. A-241 (2002) [Abstract # M952].

Watson et al., "Synergistic inhibitory effects of G17DT on gastrointestinal tumour growth in combination with cytotoxic agents," Proc. Am. Soc. Clin. Oncol. vol. 22 (2003) [Abstract # 3497].

Weinstock et al., "Binding of Gastrin$_{17}$ to Human Gastric Carcinoma Cell Lines," Cancer Research. vol. 48, No. 4 pp. 932-937 (1988).

Wendlberger et al, "The syntheses of human big gastrin I and its 32-leucine analog," Chemical Abstracts. vol. 92, No. 21 p. 722 (1980) [Abstract # 92:198749s].

Wetscher et al., "Pathophysiology of Gastroesophageal Reflux Disease," R.A. Heinder ed., R.G. Landes Co., Chapter 2 pp. 7-29 (1993).

Wong et al., "Postprandial hypergastrinaemia in patients with colorectal cancer," Gut. vol. 32 pp. 1352-1354 (1991).

Wunsch, E., and Moroder, L., "Biological and Immunological Properties of Human Gastrin I Analogues," Hoppe-Syeler's Z. Physiol. Chem. vol. 363 pp. 665-669 (1982).

Yamaguchi et al., "Amino-terminal immunoreactivity of big gastrin in plasma and tumors obtained from patients with Zollinger-Ellison Syndrome," Chem. Abstracts. vol. 100 p. 373 (1984) [Abstract # 100:154661m].

Yanaihara et al. "A New Type of Gastrin Derivative and its Use for Production of Central Region-Specific Anti-Gastrin Sera," Biomedical Research. vol. 1 pp. 242-247 (1980).

Yanaihara et al. "Human Big Gastrin N-Terminal Fragment Immunoreactivity," Gut Peptides. Elsevier, North-Holland Biomed. Press, pp. 26-33 (1979).

Zeitoun, "Comparison of Omeprazole with Ranitidine in the Treatment of Reflux Oesophagitis," Scand. J. Gastroenterol. vol. 24, Suppl. 166 pp. 83-87 (1989).

Zeng et al., "Localization of PACAP Receptors on Rat Fundic ECL and D Cells," Gastroenterology. vol. 110, Suppl. 4 p. A1136 (1996) [Abstract].

Zhou et al., "Pre-and Postoperative Sequential Study on the Serum Gastrin Level in Patients with Lung Cancer," Journal of Surgical Oncology. vol. 51 pp. 22-25 (1992).

"Development and Activity of 5-FU," CancerQuest, http://www.cancerquest.org/index.cfm?page=443 (accessed on Aug. 13, 2004) 1 pg.

Ajani et al., "An Open-Label, Multinational, Multicenter Study of G17DT Vaccination Combined with Cisplatin and 5-Fluorouracil in Patients with Untreated, Advanced Gastric or Gastroesophageal Cancer: The GC4 Study," Cancer. vol. 106, No. 9 pp. 1908-1916 (2006).
Bailey, "Radioimmunoassay of Peptides and Proteins," Methods in Molecular Biology. vol. 32 pp. 449-459 (1994).
Brinton et al., "Cancer risk following pernicious anaemia," Br. J. Cancer. vol. 59, No. 5 pp. 810-813 (1989).
Budavari et al., The Merck Index (11$^{th}$ ed.), Rahway, New Jersey, Merck & Co., p. 1082 (1989).
Burkitt et al., "Importance of gastrin in the pathogenesis and treatment of gastric tumors," World J. Gastroenterol. vol. 15, No. 1 pp. 1-16 (2009).
Cole, "Immunoassay of human chorionic gonadotropin, its free subunits, and metabolites," Clinical Chemistry. vol. 43, No. 12 pp. 2233-2243 (1997).
Demeester et al., "Patterns of Gastroesophageal Reflux in Health and Disease," Ann. Surg. vol. 184, No. 4 pp. 459-469 (1976).
Dickinson, C.J., and Yamada, T., "Gastrin-amidating Enzyme in the Porcine Pituitary and Antrum," The Journal of Biological Chemistry. vol. 266, No. 1 pp. 334-338 (1991).
Du et al. "Biochip as a potential platform of serological interferon cc2b antibody assay," Journal of Biotechnology. vol. 106, No. 1 pp. 87-100 (2003).
Gilliam, A.D., and Watson, S.A., "G17DT: an antigastrin immunogen for the treatment of gastrointestinal malignancy," Expert Opinion Biol. Ther. vol. 7, No. 3 pp. 397-404 (2007).
Gilliam et al., "A phase II study of G17DT in gastric carcinoma," EJSO. vol. 30 pp. 536-543 (2004).
He, A.R., and Marshall, J.L., "Clinical experiences with G17DT in gastrointestinal malignancies," Expert Rev. Anticancer Ther. vol. 6, No. 4 pp. 487-492 (2006) [Abstract].
Hsi, "A Practical Approach for Evaluating New Antibodies in the Clinical Immunohistochemistry Laboratory," Arch. Pathol. Lab. Med. vol. 125 pp. 289-294 (2001).
International Preliminary Examination Report corresponding to International Patent Application No. PCT/US1999/010734 dated Dec. 9, 2000.
International Preliminary Report on Patentability corresponding to International Patent Application No. PCT/US2004/09666 dated Jan. 19, 2006.
International Preliminary Report on Patentability corresponding to International Patent Application No. PCT/US2005/002793 dated Aug. 7, 2007.
Janeway et al. "Immunobiology: The Immune System in Health and Disease," Fourth Edition, Elsevier Science Ltd./Garland Publishing, New York, NY p. 544 (1999).
Jonsson, A., and Dockray, G.J., "Immunohistochemical localization to pyloric antral G cells of peptides derived from porcine preprogastrin," Regulatory Peptides. vol. 8 pp. 283-290 (1984).
Kuipers et al., "Atrophic Gastritis and Helicobacter pylori Infection in Patients with Reflux Esophagitis Treated with Omeprazole or Fundoplication," New England Journal of Medicine. vol. 334, No. 16 pp. 1018-1022 (1996).
National Institutes of Health Publication No. 99/4546, "Barrett's Esophagus," National Digestive Diseases Information Clearinghouse. pp. 1-3 (May 1999).
Notice of Acceptance corresponding to Australian Patent Application No. 2005228897 dated Nov. 25, 2009.
International Search Report corresponding to International PCT/US1990/000520 dated May 21, 1990.
International Search Report corresponding to International Patent Application No. PCT/US1999/010751 dated Oct. 19, 1999.
International Search Report corresponding to International Patent Application No. PCT/US2004/009666 dated Nov. 8, 2004.
International Search Report corresponding to International Patent Application No. PCT/US2005/010532 dated Feb. 8, 2006.
Official Action corresponding to Australian Patent Application No. 199940798 dated Jul. 13, 2001.
Official Action corresponding to Australian Patent Application No. 199940798 dated Jul. 24, 2003.
Official Action corresponding to Australian Patent Application No. 2004225437 dated Dec. 15, 2009.
Official Action corresponding to Australian Patent Application No. 2005286164 dated Feb. 14, 2011.
Official Action corresponding to Canadian Patent Application No. 2,450,898 dated May 28, 2010.
Official Action corresponding to Canadian Patent Application No. 2,520,010 dated Aug. 17, 2009.
Official Action corresponding to Canadian Patent Application No. 2,561,405 dated Jul. 31, 2009.
Official Action corresponding to Chinese Patent Application No. 200580017341.9 dated Jun. 19, 2009.
Official Action corresponding to European Patent Application No. 05 784 499.5-2406 dated Jul. 8, 2010.
Official Action corresponding to European Patent Application No. 99 924 252.2-2107 dated Jul. 4, 2003.
Official Action corresponding to European Patent Application No. 99 924 252.2-2107 dated Mar. 31, 2004.
Official Action corresponding to Israeli Patent Application No. 182012 dated Dec. 31, 2009.
Official Action corresponding to Japanese Patent Application No. 2006-509465 dated Oct. 21, 2009.
Official Action corresponding to U.S. Appl. No. 11/252,904 dated Jan. 8, 2009.
Official Action corresponding to U.S. Appl. No. 11/252,904 dated Oct. 26, 2009.
Official Action corresponding to U.S. Appl. No. 11/252,904 dated Jul. 20, 2010.
Official Action corresponding to U.S. Appl. No. 11/499,261 dated Apr. 26, 2011.
Ohtsu et al., "Randomized Phase III Trial of Fluorouracil Alone Versus Fluorouracil Plus Cisplatin Versus Uracil and Tegafur Plus Mitomycin in Patients With Unresectable, Advanced Gastric Cancer: The Japan Clinical Oncology Group Study (JCOG9205)," Journal of Clinical Investigation. vol. 21, No. 1 pp. 54-59 (2003).
Onorato et al., "Immunohistochemical and ELISA Assays for Biomarkers of Oxidative Stress in Aging and Disease," Annals of New York Academy of Sciences. vol. 854 pp. 277-290 (1998).
Osin, P.P., and Lakhani, S.R., "The pathology of familial breast cancer: Immunohistochemistry and molecular analysis," Breast Cancer Research. vol. 1, No. 1 pp. 36-40 (1999).
Plested et al. "ELISA," Methods in Molecular Medicine. vol. 71 pp. 243-261 (2003).
Podlecki et al., "Nuclear Translocation of the Insulin Receptor: A Possible Mediator of Insulin's Long Term Effects," The Journal of Biological Chemistry. vol. 262, No. 7 pp. 3362-3368 (1987).
Rondeel, "Immunofluorescence versus ELISA for the detection of antinuclear antigens," Expert Rev. Mol. Diagn. vol. 2, No. 3 pp. 226-232 (2002).
Tetin, S.Y., and Stroupe, S.D., "Antibodies in Diagnostic Applications," Current Pharmaceutical Biotechnology. vol. 5, No. 1 pp. 9-16 (2004).
Väänänen et al. "Non-endoscopic diagnosis of atrophic gastritis with a blood test. Correlation between gastric histology and serum levels of gastrin-17 and pepsinogen I: a multicentre study," European Journal of Gastroenterology & Hepatology. vol. 15, No. 8 pp. 885-891 (2003).
Van Cutsem et al., "Phase III Study of Docetaxel and Cisplatin Plus Fluorouracil Compared With Cisplatin and Fluorouracil As First-Line Therapy for Advanced Gastric Cancer: A Report of the V325 Study Group," Journal of Clinical Oncology. vol. 24, No. 31 pp. 4991-4997 (2006).
Vanhoefer et al., "Final Results of a Randomized Phase III Trial of Sequential High-Dose Methotrexate, Fluorouracil, and Doxorubicin Versus Etoposide, Leucovorin, and Fluorouracil Versus Infusional Fluorouracil and Cisplatin in Advanced Gastric Cancer: A Trial of the European Organization for Research and Treatment of Cancer Gastrointestinal Tract Cancer Cooperative Group," Journal of Clinical Oncology. vol. 18, No. 14 pp. 2648-2657 (2000).
Varro et al., "Discrimination between Temperature- and Brefeldin A-sensitive Steps in the Sulfation, Phosphorylation, and Cleavage of Progastrin and Its Derivatives," The Journal of Biological Chemistry. vol. 269, No. 32 pp. 20764-20770 (1994).
Written Opinion corresponding to International Patent Application No. PCT/US2004/009666 dated Nov. 7, 2004.

Official Action corresponding to Australian Patent Application No. 2005286164 dated Oct. 4, 2011.
Official Action corresponding to Chinese Patent Application No. 200580017341.9 dated Dec. 7, 2011.
Official Action corresponding to Indonesian Patent Application No. WO 00 2007 00931 dated Oct. 5, 2011.
Official Action corresponding to Israeli Patent Application No. 182012 dated Jul. 12, 2011.
Official Action corresponding to Japanese Patent Application No. 2007-506474 dated Jun. 7, 2011.
Official Action corresponding to Japanese Patent Application No. Hei10-549578 dated May 9, 2006.
Official Action corresponding to U.S. Appl. No. 09/700,329 dated Dec. 17, 2001.
Official Action corresponding to U.S. Appl. No. 09/700,329 dated Apr. 3, 2003.
Official Action corresponding to U.S. Appl. No. 09/700,402 dated Mar. 27, 2007.
Official Action corresponding to U.S. Appl. No. 09/700,402 dated Oct. 25, 2007.
Official Action corresponding to U.S. Appl. No. 10/235,236 dated Aug. 10, 2005.
Official Action corresponding to U.S. Appl. No. 10/323,692 dated Aug. 10, 2005.
Official Action corresponding to U.S. Appl. No. 10/829,137 dated Oct. 15, 2007.
Official Action corresponding to U.S. Appl. No. 11/663,126 dated Jul. 15, 2011.
Official Action corresponding to U.S. Appl. No. 12/693,127 dated Feb. 21, 2012.
Official Action corresponding to U.S. Appl. No. 13/012,433 dated Jul. 20, 2011.
Official Action corresponding to U.S. Appl. No. 13/012,433 dated Feb. 17, 2012.
Tytgat et al., "Five-Year Cimetidine Maintenance Trial for Peptic Ulcer Disease," Scandinavian Journal of Gastroenterology. vol. 25, No. 10 pp. 974-980 (1990).
Watson et al., "A comparison of the therapeutic effectiveness of gastrin neutralization in two human gastric cancer models: relation to endocrine and autocrine/paracrine gastrin mediated growth," Gut. vol. 45 pp. 812-817 (1999).
Abrahm et al., "Development and evaluation of a high affinity species and region specific monoclonal antibody to human gastrin," Gastroenterology, 86(5(2)):1012 (1984).
Aphton Biopharma BIO2005 Presentation, Jun. 19-22, Philadelphia, PA (2005), 26 pages.
Ajani et al., "Phase I and II Studies of the Combination of Recombinant Human Interferon- and 5-Fluorouracil in Patients with Advanced Colorectal Carcinoma," J. Biol. Response Mod. 8(2):140-146 (1989).
Ardill et al., "Autoantibodies to gastrin in patients with pernicious anaemia—a novel antibody," QJ Med 91:739-742 (1988).
Ausubel, ed., "Current Protocols in Molecular Biology," John Wiley & Sons, New York, pp. 11.15.1-11.15.4. (1990).
Azuma et al., "Immunocytochemical evidence for differential distribution of gastrin forms using region-specific antibodies," Gastroenterologia Japonica 21(4):319-324 (1986).
Baldwin, G.S. and A. Shulkes, "Gastrin, gastrin receptors and colorectal carcinoma," Gut, 42:581-584 (1998).
Belani, "Paclitaxel and Docetaxel Combinations in Non-Small Cell Lung Cancer," Chest 117:144-151 (2000).
Biagini et al., "The human gastrin/cholecystokinin receptors: Type B and type C expression in colonic tumours and cell lines," Life Sciences 61(10):1009-1018 (1997).
Blackmore, M., et al. "Autocrine growth stimulation of human renal Wilms' tumour G401 cells by a gastrin-like peptide," International Journal of Cancer 57:385-391 (1994).
Bock et al., "Benzodiazepine, gastrin and brain cholecystokinin receptor ligands: L-365,260," J. Med. Chem. 32:13-17 (1989).
Bold et al., "Gastrin stimulates growth of human colon cancer cells via a receptor other than CCK-A or CCK-B," Biochemical and Biophysical Research Communications 202(3):1222-1226 (1994).

Boon, T., "Toward a Genetic Analysis of Tumor Rejection Antigens," Advanced Cancer Research, 58:177-210 (1992).
Bruns et al. "Therapy of Human Pancreatic Carcinoma Implants by Irinotecan and the Oral Immunomodulator JBT 3002 is Associated with Enhanced Expression of Inducible Nitric Oxide Synthase in Tumor-Infiltrating Macrophages," Cancer Research 60:2-7 (2000).
Buchan, A., et al., "Regulatory peptides in Barrett's esophagus," Journal of Pathology 146(3):227-234 (1985).
Burris III et al., "Improvements in survival and clinical benefit with gemcitabine as first-line therapy for patients with advanced pancreas cancer: a randomized trial," J. Clinical Oncology 15(6):2403-2413 (1997).
Caplin et al., "Serum gastrin levels and identification of CCK-B-gastrin receptor following partial hepatectomy for liver tumours in man," Gastroenterology 110(4 suppl.) A1162 (1996).
Caplin et al., "Expression and processing of gastrin in pancreatic adenocarcinoma," Brit. J. Surgery 87:1035-1040 (2000).
Caplin et al., "Expression and processing of gastrin in hepatocellular carcinoma, fibromellar carcinoma and cholangiocarcinoma," Journal of Hepatology, 30(3):519-526 (1999).
Caplin et al., "Demonstration of new sites of expression of the CCK-B/gastrin receptor in pancreatic acinar AR42J cells using immunoelectron microscopy," Regulatory Peptides 84(1-3):81-89 (1999).
Caplin et al., "Effect of gastrin and anti-gastrin antibodies on proliferation of hepatocyte cell lines," Digestive Diseases and Sciences 46(7):1356-1366 (2001).
Casper et al., "Phase II trial of gemcitabine (2,2'-difluorodeoxycitidine) in patients with adenocarcinoma of the pancreas," Invest New Drugs 12(1):29-34 (1994) (Abstract).
Ciccotosto et al., "Expression, processing, and secretion of gastrin in patients with colorectal carcinoma," Gastroenterology 109(4):1142-1153 (1995).
Clerc et al., "Differential Expression of the CCK-A and CCK-B/Gastrin Receptor Genes in Human Cancers of the Esophagus, Stomach, and Colon," Int. J. Cancer 72:93'1-936 (1997).
"Clinical trial initiated with chemorefractory patients," Cancer Weekly, The Gale Group, (2001).
"Gastrin 17 immunogen Aphton begins combination study," R & D Focus Drug News, IMS World Publications (2000).
"Clinical trials update," Scrip, Informa UK Ltd. 2547:25 (2000).
"Other news to note," Bioworld Today, American Health Consultants Inc. 11(82) (2000).
Del Valle et al., "Progastrin and its glycine-extended post-translational processing intermediates in human gastrointestinal tissues," Gastroenterology 92:1908-1912 (1987).
Dethloff et al., "Inhibition of gastrin-stimulated cell proliferation by the CCK-B/gastrin receptor ligand C1-988," Food. Chem. Toxicol. 37:105-110 (1999).
DeWeerth et al., "Human pancreatic cancer cell lines express the CCKB/gastrin receptor," Gastroenterology A289 (1994).
de Weerth et al., "Human pancreatic cancer cell lines express the CCKB receptor," Hepatogastroenterology 46:472-478 (Jan.-Feb. 1999).
Dockray et al., "Gastric endocrine cells: gene expression, processing, and targeting of active products," Physiological Review 76(3):767-798 (1996).
Douziech et al. "Growth effects of regulatory peptides and intracellular signaling routes in human pancreatic cancer cell lines," Endocrine 9:171-183 (1998).
Dufresne et al., "Cholecystokinin and Gastrin Receptors," Physiol Rev. 86:805-847 (2006).
Ezzell, C., "Cancer 'Vaccines': An Idea Whose Time as Come?," Journal of NIH Research, 7:46-49 (1995).
Finley et al., "Expression of the gastrin gene in the normal human colon and colorectal adenocarcinoma," Cancer Res.53:2919-2926 (1993).
Fourmy et al., "Relationship of CCK/gastrin receptor binding to amylase release in dog," Regulatory Peptides 10:57-68 (1984).
Frucht et al., "Characterization of functional receptors for gastrointestinal hormones on human colon cancer cells," Cancer Research 52(5):1114-1122 (1992).

Ardis R&D Profile, "Gastrin 17 vaccine—Aphton: Anti-gastrin 17 immunogen, G17DT," Biodrugs 17(3):223-225 (2003).
Gocyk, W., et al., "Helicobacter pylori, gastrin and cyclooxygenase-2 in lung cancer," Medical Science Monitor, 6(6):1085-1092 (2000).
Grider, "Distinct receptors for cholecystokinin and gastrin," Am. J. Physiol. 259:G184-G190 (1990).
Gupta, R. and G. Siber, et al., "Adjuvants for human vaccines—current status, problems and future prospects," Vaccine, 13(14):1263-1276, (1995).
Gura, T., "Systems for Identifying New Drugs Are Often Faulty," Science, 278(5340):1041-1042, (1997).
Halter et al., "Evaluation of a monoclonal anti-gastrin antibody as a tool for immunoneutralization of gastrin during omeprazole treatment in the rat", Gastroenterology 96(5) part 2:A194 (1989).
Harris et al., "An antiapoptotic role for gastrin and the gastrin/CCK-2 receptor in Barrett's esophagus," Cancer Res. 64(6):1915-1919 (2004).
Harrison's Principles of Internal Medicine, 13th edition, Isselbacher et al. (Eds.), New York: McGraw-Hill, Inc., pp. 1690-1691 (1994).
Heinemann et al., "Cellular elimination of 2',2'-difluorodeoxycytidine 5'-Triphosphate: a mechanism of self-potentiation," Cancer Res. 52:533-539 (1992).
Helander et al., "Immunohistochemical localization of gastrin/CCK-B receptors in the dog and guinea-pig stomach," Acta Physiologica Scandinavica, 159:(4)313320 (1997).
Hellmich et al., "Human colorectal cancers express a constitutively active cholecystokinin-B/gastrin receptor that stimulates cell growth," Journal of Biological Chemistry 275(41):32122-32128 (2000).
Herbert et al. "The Dictionary of Immunology", 4th Ed. Academic Press, London, pp. 26-27 (1995).
Herbert et al. (Eds.) "The Dictionary of Immunology," 3rd Ed. Academic Press, London, p. 41, (1995).
Herget et al., "Cholecystokinin stimulates Ca2+ mobilization and clonal growth in small cell lung cancer through CCKA and CCKB/gastrin receptors," Annals of the New York Academy of Sciences 713:283-297 (1994).
Hoosein et al., "Anti-proliferative effects of gastrin receptor antagonists and antibodies to gastrin on human colon carcinoma cell lines," Cancer Res.48:7179-7183 (1988).
Hoosein et al., "Evidence for Autocrine Growth Stimulation of Cultured Colon Tumor Cells by a Gastrin/Cholecystokinin-like Peptide," Experimental Cell Research 186(1):15-21, (1990).
Huang et al., "Termination of DNA synthesis by 9-b-D-Arabinofuranosyl-2-flouroadenine," J. Biol. Chem. 265(27):16617-16625 (1990).
Hughes et al., "Development of a class of selective cholecystokinin type B receptor antagonists having potent anxiolytic activity," Proc. Natl. Acad. Sci. 87:6728-6732 (1990).
Iwase et al., "Regulation of growth of human gastric cancer by gastrin and glycine-extended pro-gastrin," Gastroenterology 113:782-790 (1997).
Jain, R., "Barriers to drug delivery in solid tumors," Scientific American, 171(1):58-65 (1994).
Kaufmann et al., "Cholecystokinin B-type receptor signaling is involved in human pancreatic cancer cell growth," Neuropeptides 31(6):573-583 (1997).
Kelley et al., "Antitumor activity of a monoclonal antibody directed against gastrin-releasing peptide in patients with small cell lung cancer," Chest 112:256-261 (1997).
Kobori et al., "Growth response of rat stomach cancer cells to gastro-entero-pancreatic hormones," Int. J. Cancer 30:65-67 (1982).
Kochman et al., "Post-translational processing of gastrin in neoplastic human colonic tissues," Biochemical and Biophysical Research Communications 189(2):1165-1169 (1992).
Koh et al., "Glycine-Extended Gastrin Promotes the Growth of a human hepatoma cell line," Gastroenterology 110(4): 1089 (1996).
Kohler et al., "Continuous cultures of fused cells secreting antibody of predefined specificity," Nature 256:495-497 (1975).
Kothary et al., "Identification of gastrin molecular variants in gastrinoma syndrome," Regulatory Peptides 17:71-84 (1987).

Kopin et al. "Expression, cloning and characterization of the canine perietal cell gastrin receptor," Proc. Natl. Acad. Sci. USA 89:3605-3609 (1992).
Kovacs et al., "Gastrin partially mediates insulin-induced acid secretion in dogs," Peptides 17(4):583-587 (1996).
Landis et al., "Cancer Statistics," Ca Cancer J. Clin. 48:6-29 (1998).
Lawrence, et al. "Radiosensitization of pancreatic cancer cells by 2',2'-Difluoro-2'-Deoxycytidine," Int. J. Radiation Oncology Biol. Phys. 34(4):867-872 (1996).
Li et al., "Induction of growth inhibition and apoptosis in pancreatic cancer cells by auristatin-PE and gemcitabine," J. Mol. Med. 3:647-653 (1999).
MacKenzie et al., "Development of a radioligand binding assay to characterize gastrin receptors in the human gastrointestinal tract," Gut 38:A37 (Abstract T146) (1996).
Mandair et al., "Cholecystokinin receptors in human pancreatic cancer cell lines," Eur. J. Cancer 34:1455-1459 (1998).
Marino et al. "Expression and post-translational processing of gastrin in heterologous endocrine cells" J. Biol. Chem. 266(10):6133-6136 (1991).
McRae et al., "Role of gastrin and gastrin receptors in the growth of human colon carcinoma cells" J. Cell Biol. 103(22a): 74 (1986).
McWilliams et al., "Antibodies raised against the extracellular tail of the CCKB/gastrin receptor inhibit gastrin-stimulated signaling," Regulatory Peptides 99(2-3):157-161 (2001).
McWilliams et al., "Coexpression of Gastrin and Gastrin Receptors (CCK-B and CCK-B) in gastrointestinal tumour cell lines," Gut 42:795-798 (1998).
Miyake, "A truncated isoform of human CCK-B/gastrin receptor generated by alternative usage of a novel exon," Biochem. Biophys. Commun. 208(1):230-237 (1995).
MSNBC News Services, "Mixed results on new cancer drug," Nov. 9, 2000 (4 pages).
Moody et al., "GRP receptors are present in non small cell lung cancer cells," Journal of Cellular Biochemistry Supplement 24:247-256, (1996).
Mulholland et al., "Elevated Gastric Acid Secretion in Patients with Barrett's Metaplastic Epithelium," Digestive Diseases and Sciences 34(9):1329-1334 (1989).
Negre et al., "Autocrine stimulation of AR4-2J rat pancreatic tumour cell growth by glycine-extended gastrin," Int. J. Cancer 66(5):653-658 (1996).
Nemeth et al., "Identification of progastrin derived peptides in colorectal carcinoma extracts," Gut 34:90-95 (1993).
Ochiai et al., "Growth-promoting effect of gastrin on human gastric carcinoma cell line TMK-1" Japan J. Can. Res. 76:1064-1071 (1985).
Ohkura et al., "Gastrin-enhanced tumor growth of a xenotransplantable human gastric carcinoma in nude mice," Jpn. J. Clin. Oncol. 10(2):255-263 (1980).
Ohning et al., "Gastrin mediates the gastric mucosal proliferative response to feeding," American Journal of Physiology 271(3(1)):G470-G476, (1996).
Okada et al., "Evaluation of cholecystokinin, gastrin, CCK-A receptor and CCK-B/gastrin receptor gene expressions in gastrin cancer," Cancer Letters 106(2):257-262 (1996).
Osband et al., "Problems in the investigational study and clinical use of cancer immunotherapy," Immunology Today 11:193-195 (1990).
Pegram et al., "Antibody dependent cell-mediated cytotoxicity in breast cancer patients in Phase III clinical trials of a humanized anti-HER2 antibody," Proc. Am. Assoc. Cancer Res. 38:602 (1997).
Rahier et al., "Biosynthesis of Gastrin. Localization of the recursor and peptide products using electron microscopic-immunogold methods," Gastroenterology 92:1146-1152 (1987).
Rehfeld et al., "Cell-specific processing of pro-cholecystokinin and pro-gastrin," Biochimie 70:25-31 (1988).
Rehfeld et al., "Residue-specific immunochemical sequence prediction" Journal of Immunological Methods 171:139-142 (1994).
Rehfeld et al., "Gastrin in human bronchogenic carcinomas: constant expression but variable processing of progastrin," Cancer Res. 49:2840-2843 (1989).
Rehfeld, J.F., "Gastrin and Colorectal Cancer: A Never-Ending Dispute," Gastroenterology 108(4):1307-1310 (1995).

Rehfeld, J.F., "Three Components of Gastrin in Human Serum," Biochem. Biophys. Acta 285:364-372 (1972).
Roberston et al., "Effect of gastrointestinal hormones and synthetic analogues on the growth of pancreatic cancer," Int. J. Cancer 63:69-75 (1995).
Rodriguez-Lescure et al., "Phase II Study of Gemcitabine (GEM) and Weekly 48 Hour Continuous Infusion (CI) with High Dose 5-Fluorouracil in Advanced Exocrine Pancreatic Cancer (APC)," Proceedings of the Annual Meeting of the American Society of Clinical Oncology 18:298 abstract 1145 (1999).
Romani et al., "Potent new family of gastrin receptor antagonists (GRAs) produces in vitro and in vivo inhibition of human colorectal cancer cell lines," Procs. AACR, 35:397 (Abstract) (1994).
Rothenberg et al., "A phase II trial of gemcitabine in patients with 5-FU-refractory pancreas cancer," Annals of Oncology 7:347-353 (1996).
Schmitz et al., "CCK-B/gastrin receptors in human colorectal cancer," European J. Clinical Investigation 31:812-820 (2001).
Scemama et al., "Characterization of gastrin-receptors on a rat pancreatic acinar cell line (AR4-2J). A possible model for studying gastrin mediated cell growth and proliferation," Gut 28:233-236 (1987).
Senior, "Immunization blocks gastrin's ability to promote tumour cell division," Drug Disc. Today 6(2):62-63 (2001).
Seva et al, "Growth-promoting effects of glycine-extended progastrin" Science, 265:410-412 (1994).
Shewach et al., "Metabolism of 2',2'-Difluoro-2'-Deoxycytidine and radiation sensitization of human colon carcinoma cells," Cancer Res. 54:3218-3223 (1994).
Shewach et al., "Radiosensitization of human solid tumor cell lines with gemcitabine" Seminars in Oncology 23(5):65-71 (1996).
Singh et al., "Gut hormones in colon cancer: past and prospective studies," Cancer J. 3:28-33 (1990).
Singh et al., "Incomplete processing of progastrin expressed by human colon cancer cells: roles of noncarboxyamidated gastrins," The American Physiological Society G459-G468 (1994).
Smith et al., "Antisense oligonucleotides to gastrin inhibit growth of human pancreatic cancer," Cancer Lett. 135:107-112 (1999).
Smith et al., "Sensitivity of the esophageal mucosa to pH in gastroesophageal reflux disease," Gastroenterology 96:683-689 (1989).
Smith et al. "Gastrin regulates the growth of human pancreatic cancer in a tonic and autocrine fashion," Amer. J. Physiol. 270(5):R1078-R1084 (1996).
Smith et al. "Identification of gastrin as a growth peptide in human pancreatic cancer", Amer. J. Physiol. 268:R135-R141 (1995).
Smith et al., "Characterization of the CCK-C (cancer) receptor in human pancreatic cancer," Int. J. Mol. Medicine 10(6):689-694 (2002).
Smith, A.M. and S.A. Watson, "Review article: gastrin and colorectal cancer," Alimentary Pharmacology & Therapeutics 14:1231-1247, (2000).
Smith et al., "Gastrin and gastrin receptor activation: an early event in the adenoma-carcinoma sequence," Gut 47(6):820-824 (2000).
Smith et al., "Gastrin may have an autocrine/paracrine role in Barrett's oesophagus and oesophageal adenocarcinoma," British Journal of Surgery 84:706-707 (1997).
Smith et al., "Gastric carcinoid expresses the gastrin autocrine pathway," British Journal of Surgery, 85:1285-1289 (1998).
Smith et al., "Phase I/II study of G17-DT, an anti-gastrin immunogen, in advanced colorectal cancer," Clinical Cancer Research 6(12):4719-4724 (2000).
Soll et al., "Gastrin-receptors on isolated canine parietal cells," J. Clin. Invet. 73:1434-1447 (1984).
Song et al., "The human gastrin/cholecystokinin type B receptor gene: alternative splice donor site in exon 4 generates two variant mRNAs," Proc. Natl. Acad. Sci. 90(19):9085-9089 (1993).
Spitler, L., "Cancer Vaccines: The Interferon Analogy," Cancer Biotherapy, 10:1-3, (1995).
Stepan et al., "Glycine-extended gastrin exerts growth-promoting effects on colon cancer cell lines," Gastroenterology 110(4):A1122 (1996).
Stubbs et al., "Endocytosis of anti-CCK-B/Gastrin receptor antibody and effect on hepatoma cell lines," J. Histochemistry Cytochemistry 50(9):1213-1217 (2002).
Stubbs et al., "Correlation between uptake of labelled anti-CCKB/gastrin receptor antibodies and the occurrence of apoptosis in hepatoma cell lines," Gastroenterology 122(4 Suppl. 1):A-380 (2002).
Sugano, et al. "Identification and characterization of glycine-extended post translational processing intermediates of progastrin in porcine stomach," J. of Biological Chemistry 260: 11724-11729 (1985).
Takinami et al., "YF476 is a new patent and selective gastrin/cholecystokinin-B receptor antagonist in vitro and in vivo," Ailment. Pharmacol. Ther. 11(1):113-120 (1997).
Tang et al., "Expression of receptors for gut peptides in human pancreatic adenocarcinoma and tumor-free pancreas," Brit. J. Cancer 75(10):1467-1473 (1997).
Taniguchi et al., "Cholecystokinin-B/gastrin receptor signaling pathway involve styrosine phosphorylatins of pI25FAK and p42MAP" Oncogene 9:861-867 (1994).
Tarasova et al., "Anti-peptide antibodies specific for the gastrin-cholecystokinin-B receptor," Letters in Peptide Science 1:221-228 (1995).
Tarasova et al., "Endocytosis of gastrin in cancer cells expressing gastrin/CCK-B receptor" Cell and Tissue Research, 287:325-333 (1997).
Thorndyke, M. and G.J. Dockray, "Identification and localization of material with gastrin-like immunoreactivity in the neutral ganglion of a photochordate, ciona intestinalis," Regulatory Peptides 16:269-279 (1986).
Todisco et al., "Gastrin and glycine-extended progastrin processing intermediates induce different programs of early gene activation," J. Biol. Chem. 279:28337-28341 (1995).
Torosian et al., "Colon carcinoma metastatic to thigh—an unusual site of metastasis. Report of a case," Diseases of the Colon and Rectum 30(10):805-808 (1987).
Tschmelitsch et al., "Enhanced antitumor activity of combination radioimmunotherapy (131I-labeled monoclonal antibody A33) with chemotherapy (fluorouracil)," Cancer Res. 57:2181-2186 (1997).
Ullrich et al. "Signal transduction by receptors with tyrosine kinase activity," Cell 61:203-212 (1990).
Upp et al., "Clinical significance of gastrin receptors in human colon cancers," Cancer Res. 49:488-492 (1989).
Van-Solinge et al., "Expression but incomplete maturation of progastrin in colorectal carcinomas," Gastroenterology 104:1099-1107 (1993).
Wank et al., "Brain and gastrointestinal cholecystokinin receptor family: structure and functional expression," Proc. Nat. Acad. Sci. 89:8691-8695 (1992).
Wank "Cholecystokinin receptors (editorial)," Am. J. Physiol. 269:G628-G646 (1995).
Wank et al., "Cholecystokinin receptor family. Molecular Cloning, structure, and functional expression in rat, guinea pig, and human," Ann. N.Y. Acad. Sci. 713:49-66 (1994).
Watson et al., "A comparison of an anti-gastrin antibody and cytotoxic drugs in the therapy of human gastric ascites in SCID mice," International Journal of Cancer 81(2):248-254 (1999).
Watson et al., "Antibodies raised by gastrimmune inhibit the spontaneous metastasis of a human colorectal tumour AP5LV," European Journal of Cancer 35(8):1286-1291 (1999).
Watson et al., "Antibodies targeting the amino terminal portion of the human CCKB/gastrin receptor inhibit the liver invasion of a human colonic tumor," Gastroenterology 114(4 Part 2): A701 (Abstract # G2899) (Apr. 15, 1998).
Watson et al., "Antiserum raised against an epitope of the cholecystokinin B/gastrin receptor inhibits hepatic invasion of a human colon tumor," Cancer Research 60(20):5902-5907 (2000).
Watson et al., "Detection of gastrin receptors on gastrointestinal tumors using the anti-gastrin receptor monoclonal antibody, 2CL," Gut 4:F271 (1993).
Watson et al., "Effect of gastrin neutralization on the progression of the adenoma:carcinoma sequence in the Mm mouse model of familial adenomatous polyposis," Gastroenterology 114(Supplement 1): A701 (Abstract #G2900) (Apr. 15, 1998).

Watson et al., "Gastrin: growth promoting effects on human gastric and colonic tumour cells," Br. J. Cancer 59:554-558 (1989).

Watson, S.A., et al., "Gastrin: growth enhancing effects on human gastric and colonic tumour cells," British Journal of Surgery 75(4):342-345, (1988).

Watson et al., "Gastrimmune raises antibodies that neutralize amidated and glycine-extended gastrin-17 and inhibit the growth of colon cancer" Cancer Res. 56:880-885 (1996).

Watson et al., "Inhibitory effects of the gastrin receptor antagonist (L-365,260) on gastrointestinal tumor cells," Cancer 68:1255-1260 (1991).

Watson et al., "Pre-clinical evaluation of the Gastrimmune immunogen alone and in combination with 5-fluorouracil/leucovorin in a rat colorectal cancer model," Int. J. Cancer 75(6):873-877 (1998).

Watson et al., "Anti-gastrin antibodies raised by gastrimmune inhibit growth of colorectaltumor AP5," Int. J. Cancer 61(2):233-240 (1995).

Watson et al., "Gastrin Receptors in Gastrointestinal Tumors", Medical Intelligence Unit, R.G. Landes Company, Georgetown, TX. pp. 1-99, (1993).

Watson et al., "Hypergastrinemia promotes adenoma progression in the APCMin−/+ Mouse Model of Familial Adenomatous Polyposis," Cancer Research 61:625-631 (2001).

Watson et al., "Expression of gastrin-CCKB receptor isoforms in gastrointestinal tumor cells: Relationship to gastrin secretion," Proceedings of the American Association for Cancer Research Annual Meeting 38(0):116 (Abstract 773), (1997).

Watson et al., "Gastrin antagonists and gastrointestinal tumors," Expert Opinion on Investigational Drugs 4(12):1253-1266 (1995).

Watson et al., "Antibodies targeting the Amino Terminal portion of the Human CCKB/gastrin receptor inhibit the liver invasion of a human colonic tumour," Research Presentation, Digestive Disease Week, American Gastroenterological Association (1998), 17 slides.

Watson, S. and A. Gilliam, "A new weapon in the therapeutic armoury for gastrointestinal malignancy," Expert Opinion on Biological Theory 1(2):309-317(2001).

Watson et al., "Inhibition of gastrin-stimulated growth of gastrointestinal tumour cells by octreatide and the gastrin/cholecystokinin receptor antagonists, proglumide and lorglumide," European Journal of Cancer, 28A(8-9):1462-1467, (1992).

Watson et al., "Intracellular gastrin in human gastrointestinal tumor cells," Journal of the National Cancer Institute 83:866-871 (1991).

Watson et al., "The in vitro growth response of primary human colorectal and gastric cancer cells to gastrin," International Journal of Cancer 43:692-696, (1989).

Watson et al., "Therapeutic effect of the gastrin receptor antagonist, CR2093 on gastrointestinal tumour cell growth," British Journal of Cancer 65(6):879-883, (1992).

Weinberg et al., "Cholecystokinin A and B receptors are differentially expressed in normal pancreas and pancreatic adenocarcinoma," J. Clin. Invest. 100(3):597-603 (1997).

Weiner, L., "An Overview of Monoclonal Antibody Therapy of Cancer," Seminars in Oncology 26(4)(Supp. 12):41-50 (1999).

Yuki et al., "YM022, a patent and selective gastrin/CCK-B receptor antagonist, inhibits peptone meal-induced gastric acid secretion in Heidon hair pouch dogs" Dig. Dis. Sci. 42(4):707-714 (1997).

"Disorder," Stedman's Medical Dictionary 27th Edition, 2003 http://www.thomsonhc.com/pdrel/librarian/PFDefaultActionld/pdrcommon.Stedmans (1 page).

Abbruzzese et al., "Phase I Trial of Recombinant Human—Interferon and Recombinant Human Tumor Necrosis Factor in Patients with Advanced Gastrointestinal Cancer," Cancer Research. vol. 49 pp. 4057-4061 (1989).

Bardram, "Progastrin in Serum from Zollinger-Ellison Patients: An Indicator of Malignancy?" Gastroenterology. vol. 98, No. 6 pp. 1420-1426 (1990).

Gisbert et al., "Decrease in gastrin levels after H. pylori eradication," Revista espanola de enfermedades digestivas (Spanish Journal of Gastroenterology). vol. 87, No. 2 pp. 99-107 (1995) [Abstract].

International Search Report corresponding to International Patent Application No. PCT/IB2005/002793 dated Dec. 7, 2005.

Interview Summary corresponding to U.S. Appl. No. 11/663,126 dated Nov. 15, 2011.

Mishell, B.B., and Shiigi, S.M., "Selected Methods in Cellular Immunology," Chapter 17: Immunoglobulin-Producing Hybrid Cell Lines, W.H. Freeman and Co.:San Francisco pp. 368-370 (1980).

Non Opposition Notice corresponding to European Patent Application No. 97905858.3-2401 dated Feb. 17, 2012.

Notice of Allowance corresponding to Canadian Patent Application No. 2,520,010 dated Nov. 22, 2011.

Notice of Allowance corresponding to U.S. Appl. No. 11/663,126 dated Jan. 6, 2012.

Le Meuth et al., "Differential Expression of A- and B-Subtypes of Cholecystokinin/Gastrin-Receptors in the Developing Calf Pancreas," Endocrinology. vol. 133, No. 3 pp. 1182-1191 (1993).

Ledda-Columbano et al., "Compensatory Regeneration, Mitogen-Induced Liver Growth, and—Multistage Chemical Carcinogenesis," Environmental Health Perspectives. vol. 101, No. 5 pp. 163-168 (1993).

Lee et al., "The Human Brain Cholecystokinin-B/Gastrin Receptor," The Journal of Biological Chemistry. vol. 268, No. 11 pp. 8164-8169 (1993).

Leith et al., "Effects of Partial Hepatectomy on Growth Characteristics and Hypoxic Fractions of Xenografted DLD-2 Human Colon Cancers," Radiation Research. vol. 123, No. 2 pp. 263-268 (1992).

Machine translation of JP 06107564, 1994.

Mahood et al., "Inhibition of Fluorouracil Stomatitis by Oral Cryotherapy," Journal of Clinical Oncology. vol. 9 pp. 449-452 (1991).

Makishima et al., "Active Immunization Against Gastrin-17 With an N-Terminal Derived Immunogen Inhibits Gastric and Duodenal Lesions in Rats," Gastronenterology. vol. 106, No. 4, Part. 2 p. A824 (1994) [Abstract].

Makishima et al., "Inhibition of Gastrin-17 Stimulated Acid Secretion Through Active Immunization in Rats," FASEB Journal. vol. 8, Nos. 4-5 p. A92 (1994) [Abstract # 535].

Martin et al. "Selection of Trypsin of 2 Sublines of Rat Cancer Cells Forming Progressive or Regressive Tumors," Int. J. Cancer. vol. 32 pp. 623-627 (1983).

Masseyeff, R.F., and Ferrua, B., "The Art of Assay Design in Heterologous Enzyme Immunoassay," International symposium on immunoenzymatic techniques. vol. 2 pp. 139-155 (1983).

"Clinical Study Report: G17DT," Aphton Corporation, 107 pages (Sep. 19, 2003).

Issued Patent corresponding to Canadian Patent Application No. 2,520,010 dated Jul. 10, 2012.

Notice of Acceptance corresponding to Australian Patent Application No. 2005286164 dated May 15, 2012.

Notice of Allowance corresponding to U.S. Appl. No. 12/693,127 dated Aug. 31, 2012.

Nowak et al., "Gemcitabine Exerts a Selective Effect on the Humoral Immune Response: Implications for Combination Chemo-immunotherapy," Cancer Research. vol. 62 pp. 2353-2358 (2002).

Nowak et al., "Synergy between Chemotherapy and Immunotherapy in the Treatment of Established Murine Solid Tumors," Cancer Research. vol. 63 pp. 4490-4496 (2003).

Official Action corresponding to Canadian Patent Application No. 2,580,965 dated Feb. 27, 2012.

Official Action corresponding to Chinese Patent Application No. 200580017341.9 dated Jul. 3, 2012.

Official Action corresponding to Japanese Patent Application No. 2006-310647 dated May 29, 2012.

Official Action corresponding to Japanese Patent Application No. 2011-034753 dated May 29, 2012.

Deed of Letters Patent corresponding to Australian Patent Application No. 2005286164 dated Sep. 6, 2012.

Intent to Grant corresponding to European Patent Application No. 05 784 499.5-2406 dated Aug. 13, 2012.

Issued Patent corresponding to Australian Patent Application No. 2005286164 B2 dated Sep. 16, 2012.

Notice of Preliminary Rejection corresponding to Korean Patent Application No. 10-2007-7009115 dated Mar. 30, 2012.

Official Action corresponding to Canadian Patent Application No. 2,561,405 dated Dec. 5, 2012.

Official Action corresponding to Canadian Patent Application No. 2,580,965 dated Oct. 19, 2012.
Official Action corresponding to Chinese Patent Application No. 200580036710.9 dated Apr. 16, 2012.

Official Action corresponding to U.S. Appl. No. 13/012,433 dated Sep. 25, 2012.

* cited by examiner

SEQUENCE LISTING

```
<160> NUMBER OF SEQ ID NOS: 6

<210> SEQ ID NO 1
<211> LENGTH: 17
<212> TYPE: PRT
<213> ORGANISM: Homo sapiens

<400> SEQUENCE: 1

Lys Leu Asn Arg Ser Val Gln Gly Thr Gly Pro Gly Pro Gly Ala Ser
1               5                   10                  15

Leu

<210> SEQ ID NO 2
<211> LENGTH: 15
<212> TYPE: PRT
<213> ORGANISM: Homo sapiens

<400> SEQUENCE: 2

Gly Pro Gly Ala His Arg Ala Leu Ser Gly Ala Pro Ile Ser Phe
1               5                   10                  15

<210> SEQ ID NO 3
<211> LENGTH: 7
<212> TYPE: PRT
```

```
<213> ORGANISM: Homo sapiens

<400> SEQUENCE: 3

Ser Ser Pro Pro Pro Cys
1               5

<210> SEQ ID NO 4
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 4

Glu Gly Pro Trp Leu Glu Glu Glu Glu Ala Tyr Gly Trp Met Asp
1               5                   10                  15

Phe

<210> SEQ ID NO 5
<211> LENGTH: 5
<212> TYPE: PRT
<213> ORGANISM: Homo sapiens

<400> SEQUENCE: 5

Gly Trp Met Asp Phe
1               5

<210> SEQ ID NO 6
<211> LENGTH: 34
<212> TYPE: PRT
<213> ORGANISM: Homo sapiens

<400> SEQUENCE: 6

Glu Leu Gly Pro Gln Gly Pro Pro His Leu Val Ala Asp Pro Ser Lys
1               5                   10                  15

Lys Glu Gly Pro Trp Leu Glu Glu Glu Glu Ala Tyr Gly Trp Met
            20                  25                  30

Asp Phe
```

COMBINATION TREATMENT OF PANCREATIC CANCER

This application is a continuation of U.S. application Ser. No. 11/360,378, to Philip C. Gevas, Dov Michaeli, Stephen Grimes, and Martyn Caplin, filed Feb. 22, 2006, now abandoned entitled "Combination Treatment of Pancreatic Cancer," which is a continuation of U.S. application Ser. No. 10/104,607, to Philip C. Gevas, Dov Michaeli, Stephen Grimes, and Martyn Caplin, filed Mar. 22, 2002, now abandoned entitled "Combination Treatment of Pancreatic Cancer," which claims the benefit of priority, under 35 U.S.C. §119(e) to U.S. Provisional Application Ser. No. 60/278,294, to Dov Michaeli, Martyn Caplin, Philip Gevas, and Stephen Grimes, filed on Mar. 23, 2001, entitled "COMBINATION TREATMENT OF PANCREATIC CANCER." The subject matter of each of these applications is incorporated herein in its entirety.

FIELD OF THE INVENTION

The invention relates to a combination of immunological and chemotherapeutic treatment of pancreatic cancer. In particular, treatment of locally advanced or metastatic gastrin-dependent pancreatic adenocarcinoma in the form of immunization is provided against gastrin hormone in combination with one or more anti-cancer drugs.

BACKGROUND OF THE INVENTION

In 1998, approximately 29,000 people in the United States were diagnosed with pancreatic adenocarcinoma, and approximately 28,900 people were expected to die from this tumor [1]. The overall cure rate for pancreatic cancer remains less than 5% despite more than 20 years of clinical trials. Only 10% of subjects have a potentially resectable tumor; however, even for subjects undergoing a curative pancreaticoduodenectomy, five-year survival is 6-24% [2]. The vast majority of subjects have unresectable tumors and develop metastatic disease within the first year of therapy. The median survival for subjects with metastatic disease is 3-6 months.

The description of cancertrophic agents set forth below includes both growth factor and growth factor receptors which are surprisingly expressed or overexpressed in cancerous tumors or more specifically cancer cells.

Gastrin is highly expressed in the antral mucosa and duodenal bulb and expressed at low levels in a variety of tissues, including the pancreas. Gastrin is also highly expressed in the fetal pancreas, a fact which may be of significance in the development of pancreatic neoplasms [3].

The normal nonfetal pancreas shows no expression of gastrin isoforms or receptor. It has been shown that a large percentage of patients with pancreatic cancer possess progastrin, glycine-extended gastrin, amidated gastrin in their blood, and CCK-B/gastrin receptor are present in the tumor cells [4]. Thus, it was later found that pancreatic adenocarcinoma expresses the precursor forms of gastrin, especially the progastrin and glycine-extended forms. The tumor cells were also determined to express the CCK-B/gastrin receptor. Similarly, these precursor gastrin forms and receptors were detected in other cancers, such as gastric, colonic, and hepatocellular carcinomas.

Several growth factors have been postulated to affect the growth and development of pancreatic cancer. Moreover, it is well recognized that gastrin is a trophic hormone and promotes growth of gastrointestinal (GI) and non-gastrointestinal cancers [4]. Gastrin has been shown to promote the growth of hepatocellular carcinoma, renal cell carcinoma, small cell carcinoma of the lung and also pancreatic carcinoma [6-9]. Gastrin affects cell behavior in the form of circulating fully processed peptides as well as autocrine process whereby incomplete processed precursor gastrin, especially in the form of glycine-extended gastrin can stimulate cell growth or cell function [10].

In particular, a number of investigations have shown the important role that G17 gastrin and glycine-extended G17 (Gly-G17) gastrin play in the proliferation of gastrointestinal adenocarcinomas including pancreatic adenocarcinoma. It has been demonstrated that G17 gastrin causes proliferation of a variety of colorectal, gastric and pancreatic cancer cell lines, both in vitro and in vivo [11] [12] [6] [13] and that an autocrine pathway may be involved [14] [15]. Gly-G17 gastrin has also been shown to stimulate growth of various cancers via an autocrine/paracrine pathway [16] [17].

Gastrin is actually a family of peptides including G17 gastrin, G34 gastrin, and the immature forms, glycine-extended G17 (Gly-G17) gastrin and glycine-extended G34 (Gly-G34) gastrin. G17 and G34 share a 5-amino-acid carboxy-terminal sequence in common with cholecystokinin (CCK). It has been shown that in this sequence that interacts with the CCK-B/gastrin receptor [11] [18].

Gastrin requires post-translational carboxy-terminal alpha-amidation using glycine as the amide donor. The penultimate intermediate is gastrin with a C-terminal glycine—the so-called glycine-extended gastrins (Gly-G17 and Gly-G34). Similar concentrations of glycine-extended forms and mature gastrins are often found. Gly-G17 appears to have some of gastrin's biological activities [17].

Different tissues exhibit different patterns of post-translational gastrin modification resulting in the accumulation of different intermediates. While gastrin produced by the gastric antrum is largely fully amidated G17 [19], anterior pituitary corticotrophs almost entirely fail to process the amidation site, resulting in >99% glycine-extended gastrins. In neonatal pancreatic cells, gastrin is largely in the G34 form [19] and it is fully sulfated at Tyr29, a unique modification, making it CCK-like in its potency [3]. In neoplastic tissue, immature forms of gastrin typically predominate. In colorectal carcinomas, a considerable amount of progastrin species accumulates [20] [21]. In rat pancreatic tumor AR42J, it has been reported that only glycine-extended gastrins are present [17]. Nothing has been reported on the forms of gastrin produced by human pancreatic cancer cells.

The gastrin and CCK-B receptors were recently cloned and shown to be identical [22]. Messenger RNA for CCK-B receptors was detected in all pancreatic cancer cell lines of ductal origin and in normal pancreatic tissue as well as in fresh tumor cells [23] [24] [25] and may be over-expressed in malignant pancreatic tissue in comparison with normal tissue [26]. Some authors have detected CCK-B receptors using radiolabeled ligand binding (either gastrin or CCK) technologies in both normal pancreas and tumor cell lines [27] Others have failed to detect receptors in the tumor cell lines but do detect them in normal tissue [28] [29].

MacKenzie et al. [30] demonstrated by radioligand-binding the abundant presence of CCK-B/gastrin receptor on the rat pancreatic tumor cell line, AR42J. Tarasova et al. [31] have shown that following ligand binding assays, rapid clustering and internalization of the CCK-B/gastrin receptor occurred in the pancreatic tumor cell line AR42J, as well as in a variety of human gastric and colorectal tumor cell lines. Incubation of the CCK-B/gastrin receptor with 1 nM of the specific inhibitor CI-988 inhibited the proliferation of gastrin-stimulated (1 nM) AR42J cells by about 47% after 96 hours of treatment, which is consistent with competitive inhibition of the gastrin receptor [32]. Anti-G17 antibodies have been shown to inhibit the binding of gastrin to the CCK-B/gastrin receptors on the pancreatic tumor cell line AR42J.

It has been shown that gastrin peptides increase the proliferation of GI cancer cell lines of human and animal origin both in vitro and in vivo [5]. More recent studies with four human pancreatic cell lines have shown that all proliferation was increased by 40-68% G17 gastrin relative to untreated controls. Studies with receptor antagonists showed that this proliferative effect was mediated via the CCK-B receptor [11]. Other studies have reported similar results [12], but not all studies report a positive effect even if the presence of CCK-B receptors was confirmed by binding studies [25].

Additional studies compared the mitogenic effects of gastrin on colorectal and gastric tumor cells obtained from cancer subjects at surgical resection. It was shown that cells from 69% of gastric and 55% of colorectal tumors had an enhanced proliferation in response to G17 gastrin, which was of greater magnitude than that seen in normal cells obtained from the G1 mucosa [33] [34].

It has been shown that the gastrin gene is activated in epithelial cells derived from G1 tumor specimens, but not in normal G1 mucosal cells [35] [36] [37] [21] [17] [38]. Malignant epithelial cells have been shown to produce mitogenic gastrin peptides, which can increase self-proliferation of the surrounding cells, thereby inducing a state of tumor autonomy [39][16].

Gastrin also stimulated in vivo tumor growth in mice inoculated with human Panc-1 cells. Tumor volume in mice treated with pentagastrin was 127% greater than untreated control tumors, while those animals receiving a CCK-B receptor antagonist (without pentagastrin) had tumors only 60% as large as controls [11].

The stimulatory effect of gastrin was also demonstrated by antisense RNA directed at gastrin [40] which suppressed the growth of human pancreatic cell lines. The observation that gastrin mRNA is detectable in all normal as well as tumor cell lines and in fresh pancreatic tissue, while gastrin peptide is detectable only in malignant tissue, suggested that gastrin mRNA may be translated only in the tumor cells [15].

Although inactive in stimulating acid secretion, Gly-G17 gastrin has been shown to increase the proliferation of pancreatic [41] cancer cells, G17 and Gly-G17 were found to be equipotent in stimulating proliferation of rat pancreatic tumor AR42J cells.

The normal physiological functions of gastrin are mediated by CCK-B/gastrin receptors. Expression of the receptor occurs in all types of gastrointestinal malignancies including colorectal, gastric, pancreatic, hepatomas and colorectal liver metastases [42] [43][24] [15] [44] [45] [46]. Different isoforms of the receptor exist [51] [52], and more than one isoform of the CCK-B gastrin receptor may be co-expressed on individual cells. Therefore, antagonism of CCK-B receptors may not be the optimal method to suppress the proliferative action of gastrin present either in the serum or produced locally by the tumor cells.

It has been shown that several types of tumors, e.g., colorectal, stomach, pancreatic and hepatocellular adenocarcinomas, possess CCK-B/gastrin receptors in their plasma membranes and that they respond to gastrin with powerful cellular proliferation [53] [13]. Furthermore, more recently it has been discovered that many of these cancer cells also secrete gastrin and thus effect an autonomous proliferative pathway [21] [37] [16].

The CCK-B/gastrin receptor belongs to a family of G protein-coupled receptors with seven transmembrane domains with equal affinity for both CCK and gastrin [54]. This receptor was named a CCK type-B receptor because it was found predominantly in the brain [55]. The receptor was subsequently found to be identical to the peripheral CCK/gastrin receptor in the parietal and ECL cells of the stomach [56]. This receptor has been well characterized in a number of normal [57] [58] and tumor tissues [59] [34], and extensively studied using the rat pancreatic adenocarcinoma cell line AR42J [60]. The AR42J CCK-B/gastrin receptor cDNA has been cloned and sequenced, and it is more than 90% homologous in DNA sequence to the CCK-B/gastrin receptor in rat and human brain, and more than 84% homologous in sequence to the canine parietal cell CCK-B/gastrin receptor cDNA [61], demonstrating a high sequence homology even between species.

The peptide hormones G117 and G34 bind to the CCK-B/gastrin receptor on the cell membrane of normal cells. However, it has been found that G17, and not G34, stimulates the growth of gastrin-dependent cancer cells. Serum-associated G17, in particular, has the potential to stimulate the growth of colorectal tumors in an endocrine manner mediated by CCK-B/gastrin receptors [34] in the tumor cells. Gastrin-17 appears to be particularly implicated in stimulating the growth of colorectal adenocarcinomas due to a possible increased affinity for the CCK-B/gastrin receptor on the tumor cells, over other gastrin hormone species [62]. The CCK-B/gastrin receptors were found to be expressed in a high affinity form on 56.7% of human primary colorectal tumors [53]. It has been postulated that a potential autocrine loop may also exist due to endogenous production of precursor gastrin peptides by such tumors [21]. The resulting G17 ligand/receptor complex stimulates cell growth by way of secondary messengers for regulating cell function [63]. The binding of G17 to the CCK-B/gastrin receptor leads to activation of phosphatidyl inositol breakdown, protein kinase C activation with a resultant increase in intracellular calcium ion concentration, as well as the induction of c-fos and c-jun genes via mitogen-activated protein kinase, which has been implicated in the regulation of cell proliferation [64]. Additionally, gastrin binding to the CCK-B/gastrin receptor has been associated with the subsequent increase in phosphorylation by a tyrosine kinase, pp125FADK (focal adhesion kinase), which may also have a role in the transmission of mitogenic signals [65].

A number of high affinity CCK-B/gastrin receptor antagonists have been evaluated therapeutically both in vitro and in vivo in a number of experimental models of gastrointestinal cancer. For example, proglumide, a glutamic acid derivative [16] [66] [67] Benzotript, an N-acyl derivative of tryptophan; L-365,260, a derivative of Aspercillin [68], and CI-988 a molecule that mimics the C-terminal pentapeptide sequence of CCK [69] have been shown to effectively neutralize the effects of exogenous gastrin on gastrointestinal tumor growth both in vitro and in vivo [6] [70]. However, these antagonists have severe toxic side effects and lack specificity as they block the action of all potential ligands of the receptor such as G34 and CCK in normal cells. Recently, highly potent and selective CCKB/gastrin receptor antagonists such as YM022 [71] and YF476 [72] have been also described.

Proglumide and Benzotript have been widely assessed in pre-clinical studies. The main problem with these compounds is their lack of potency, with relatively high concentrations required to displace G17. Despite this, proglumide and benzotript inhibited the basal and gastrin-stimulated proliferation of a number of cell lines [67]. In addition, proglumide increased the survival of xenograft mice bearing the gastrin-sensitive mouse colon tumor, MC26 to 39 days in the treated animals from 25 days in the control animals.

Due to the low specificity of this class of gastrin antagonizing agents for the gastrin/CCKB receptor, the inhibition of tumor growth may not be effectively control with gastrin antagonists. Moreover, the cellular receptors which recognize and bind the gastrins do not bind all the inhibitors tested [16]. Thus, if complete inhibition of gastrin binding to the receptor does not occur in the autocrine growth cascade, then the gastrin antagonists may be unable to block this mechanism of tumor growth promotion.

Recent developments have demonstrated the feasibility of immunoneutralization of hormones or their receptor moieties in order to inhibit the hormone controlled physiological functions or effects, such as cellular growth. (U.S. Pat. Nos. 5,023,077 and 5,468,494)

For example, immunization with the immunogen G17DT elicits antibodies that react specifically with the aminoterminal end of G17 gastrin and Gly-G17 gastrin (U.S. patent application Ser. No. 08/798,423). The antibodies do not cross-react with any of the other gastrin species tested, including G34 gastrin and CCK. Antibodies elicited by G17DT inhibit the binding of gastrin to the CCK-B/gastrin receptor on a variety of gastrointestinal tumor cells, including pancreatic tumor cells. Antibodies elicited by G17DT inhibit the growth of human gastric, pancreatic, and colorectal cancer cells in vitro and in in vivo animal models of gastric and colorectal cancer. Immunological neutralization has been discovered to inhibit metastsis of colorectal cancer [46] [47].

The alternate or additional immunological weapon against the gastrin effect on pancreatic cancer growth comprises the induction of anti-CCKB/gastrin receptor antibody binding with a specific anti-receptor GRE1 or GRE4 peptide epitope, as described in co-assigned pending U.S. patent application Ser. No. 09/076,372. Accordingly, the receptor moieties can be prevented from binding the circulating gastrin hormone or fragments thereof. Furthermore, this immunological inhibition of pancreatic cancer advantageously results in the internalization of the receptor antibody complex causing apoptosis-like cell death.

Certain anticancer chemical compounds have been found useful for treating adenocarcinoma such as pancreatic tumors. For example, Gemcitabine (2', 2', difluorodeoxycytidine) is a nucleoside analog with structural similarities to cytarabine. Its mode of action involves disruption of cell replication. Gemcitabine enters the cell via a carrier-mediated transport system that is shared with other nucleosides. It is phosphorylated sequentially to difluorodeoxycytidine monophosphate (diFdCMP), difluorodeoxycytidine diphosphate (diFdCDP) and difluorodeoxycytidine triphosphate (diFdCTP). Preclinical studies of gemcitabine have shown incorporation of the phosphorylated diFdCTP into DNA [73] [74].

Gemcitabine triphosphate is a substrate and competitive inhibitor of DNA polymerases alpha and epsilon. Once dFdCTP is incorporated into the growing chain, only one (or perhaps two) more nucleotide(s) can be incorporated, a novel mechanism termed "masked chain termination." Once additional residues are incorporated at the 3' end, gemcitabine cannot be excised by the proofreading exonucleolytic activity of DNA polymerase [48]. DNA fragmentation and apoptosis follow. As predicted by its mode of action, gemcitabine is active only in S-phase when cells are actively replicating DNA [49].

Since pancreatic cancer has a high occurrence of metastasis, this method also comprises advantageous combination treatment with immunological anti-gastrin, anti-CCK-B/gastin receptor agents and chemotherapeutic agents such as irinotecan and optionally 5-FU/LV or gemcitabine, or both.

Irinotecan is a chemotherapeutic drug (CAMPOSAR), which has been approved for some types of cancer, mostly as second-live treatment. It has been applied in conjunction with 5-FU/LV against metastatic colorectal carcinoma which progressed after 5-FU treatment.

Cisplatin is a drug used in a variety of neoplasms that is capable of producing inter- and intrastrand DNA cross-links. Cisplatin can be administered alone or together with other chamotherapeucics.

In view of the very poor prognosis of pancreatic cancer and lack of significant survival afforded by the currently available therapies, a therapeutic strategy involving immunological targeting of gastrin and its receptor in combination with chemotherapeutic methods using one or more chemotherapeutic agents may provide a novel and efficacious therapy.

SUMMARY OF THE INVENTION

Contrary to expectations, it has now been discovered that the immune response to vaccination of the treated animal or human is not significantly repressed by chemotherapeutics, or at least can be overcome by adjusting the vaccine dosage.

Advantageously, therefore, the present invention provides a treatment of pancreatic cancer comprising combining immunotherapy with one or more than one anticancer growth active immunogen and chemotherapy wherein the chemotherapy comprises one or more chemotherapeutic anticancer agent.

The invention provides a combination of methods for use in the treatment of pancreatic cancer including metastatic tumors thereof, wherein the immunotherapy is administered both in the form of an active or passive immunological composition comprising one or more cancer trophic target and the chemotherapy comprise one or more chemotherapeutic agent suitable for the inhibition of cancer growth. In the general context of this invention, the active immunization comprises an anti-growth factor immunogen and/or an anti-growth factor receptor immunogen, and the passive immunization comprises anti-growth factor antibodies, and anti-growth factor receptor antibodies which are polyclonal or monoclonal.

In particular, the combination of methods provides treatment of pancreatic cancer by immunological therapy directed against hormones and receptors thereof which stimulate the growth of pancreatic cancer cells, and concomitantly by administration of pharmaceutically acceptable chemotherapeutic agents.

The invention also provides a combination of treatment of pancreatic cancer comprising administering an immunogenic composition containing a conjugate of the amino-terminal G17 peptide epitope covalently linked to an immunogenic carrier proteins and a chemotherapeutic composition.

One form of active immunization according to the invention provides an antigastrin effective immunogenic composition comprising an epitope of the gastrin peptide G17 which is covalently linked through a spacer peptide to an immunogenic carrier or immunogenic carrier fragment.

More particularly, the invention may provide a conjugate of the aminoterminal G17 peptide epitope linked to a seven amino acid peptide spacer, the spacer being attached to an ε-amino acid carrying side chain of the lysine residue of diphtheria toxoid and a chemotherapeutic composition carrier protein.

The immunogenic composition according to this invention contains a dosage in units ranging from approximately 10 μg to 5000 μg of immunogen.

An alternate embodiment of the invention provides an antigastrin receptor immunogen. For example, such an embodiment provides an immunogen which comprises a CCKB/gastrin receptor peptide or fragment thereof which elicits antibodies in the immunized patient, wherein the antibodies are specifically directed against an epitope of the receptor so as to bind and inactivate the receptor.

The antibodies produced by the anti-CCK-B/gastrin receptor immunogens thereby inhibit the growth stimulatory pathway, including the autocrine growth-stimulatory pathway of tumor cells and ultimately the growth of the tumor.

Another embodiment of the invention provides an immunogen which elicits an auto-antibody specifically directed to a gastrin receptor, such that upon binding the antibody is internalized into the receptor associated pancreatic tumor cell.

A further embodiment of the invention provides for an immunogen which elicits an antibody specifically directed to the gastrin receptor, or fragment thereof, such that upon binding the antibody is internalized into the nucleus of the receptor associated pancreatic tumor cell.

An embodiment of the treatment of pancreatic cancer provides immunization with an anti-CCKB/gastrin receptor immunogen, alone/or combined with treatment for the cancer by administering a composition comprising one, or more than one, chemotherapeutic agent effective against pancreatic cancer.

A further embodiment of the invention advantageously provides an immunogenic composition formulated as a water-in-oil emulsion amenable for intramuscular injection.

Another embodiment of the treatment of pancreatic cancer provides immunization with both anti-gastrin immunogen and anti-gastrin receptor immunogen combined with one, or more than one, chemotherapeutic agent.

The treatment according to the invention combines the immunological phase of therapy with one or more chemical adjuvant compounds selected from known pharmaceutically acceptable taxanes, such as e.g. docetaxel, taxotere, Paclitaxel, 7-Epi-Taxol, 10-Deacetyl Taxol, as well as mixtures thereof, 5-fluorouracil (5-FU), cisplatin, gemcitabine, irinotecan (also called CAMPOSAR or CPT-11), and tamoxifen 5-FU may be administered with leucovorin.

The chemotherapy comprises doses of 5-FU ranging from 50 to 1000 mg/m$^2$/d, with leucovorin at 90 mg/d to 100 mg/d or irinotecan ranging from 200-300 mg/m.sup.2/d, gemcitabine ranging from 100-1500 mg/m.sup.2/d; cisplatin (platinol) ranging from 40 mg-100 mg/m.sup.2/d; and tamoxifen from 10 mg-20 mg tablet per day. For example, combinations of chemotherapeutic agents comprise 5-FU Cisplatin, 5-FU-Gemcitabine or 5-FU with leucovorin & cisplatin.

The invention provides a treatment of G17DT immunogen (100-500 μg) in combination with gemcitabine of unresectable metastatic carcinoma of the pancreas in previously untreated subjects.

In accordance with this invention, the method of treatment of pancreatic cancer provides periodic administration of immunological anti-growth stimulating agents in conjunction with a chemotherapeutic agent comprising one or more chemical compounds having an anti-cancer effect. The immunological agents are either hormone immunogens for active immunization or passive immunization with exogenous anti-growth factor antibodies. The exogenous human antibodies can be produced in transgenic animals or other suitable subjects using standard techniques. For passive immunization, the antibodies can be monoclonal, polyclonal or a hybrid. The antibodies are administered in purified form, such as, e.g. IgG fractions, comprising dosages sufficient to neutralize the circulating growth factors or hormones, e.g., gastrin G17 or Gly-G17, or their receptors.

A further growth factor or hormone specific embodiment of the invention utilizes the exogenously added anti-CCKB/gastrin receptor antibody in modified form with agents such as toxins, or radiolabelled substances. The toxin can be of the cholera type. The radiolabel can be $^{125}$Iodine, $^{131}$Iodine, $^{187}$Rhenium or $^{90}$Yttrium.

For example, the embodiment provides a radiolabelled specific anti-cancertrophic antibody to destroy the cell upon internalization further in combination with other chemotherapeutic and other immunologically active agents.

Radiolabeled antibodies can also be used for detection diagnoses wherein the radiolabel comprises $^{125}$Iodine, $^{131}$Iodine, Technetium ($T_c$), $^{111}$Indium, $^{67}$Gallium, or $^{90}$Yttrium.

DETAILED DESCRIPTION OF THE INVENTION

Anti-G17DT antibodies administered in animals with xenotransplants of various cancers, as well as antibodies elicited by active immunization of subjects with colorectal or stomach cancer with G17DT conjugate, bound both G17 and Gly-G17 gastrins at high affinity. Furthermore, safety and dose ranging studies in subjects with advanced colorectal, stomach, and pancreatic cancers have demonstrated that high-affinity antibodies are elicited by G17DT immunogen. Biological therapies such as immunization with G17DT in combination with chemotherapy may show a higher degree of efficacy than each alone. The higher efficacy is due to the inhibition of a proliferative factor such as gastrin, is cytostatic, and the chemotherapy is a cytotoxic effect. A combination of the two modalities is synergistic, similarly as previously demonstrated with anti-HER2 antibody treatment in combination with chemotherapy in advanced breast cancer [75] and which, more specifically, is shown by results of pre-clinical studies of combinations of G17DT with chemotherapeutic agents.

The majority of neutralizing antisera raised against gastrin peptides has been directed against the 5-amino-acid carboxy-terminal portion of the molecule common to G17 gastrin (SEQ ID NO: 4), G34 gastrin (SEQ ID NO: 5), and cholecystokinin (CCK). This carboxy-terminal sequence of these peptide hormones interacts with the CCK-B/gastrin receptor [14]. G17DT conjugate was developed in an attempt to generate antibodies against the amino-terminal end of G17 and Gly-G17 gastrins. G17DT conjugate is constructed from a synthetic 16-residue peptide comprising an epitope derived from the amino acid residue 1-9 of G17 gastrin linked at the C-terminal to a 7 amino acid residue spacer peptide terminating in a cysteinyl residue. The peptide is cross-linked via its C-terminal cysteine residue to a carrier protein, Diphtheria toxoid (DT), using the bifunctional cross-linker EMCS to form the G17DT conjugate. G17DT has been formulated in a water-in-oil emulsion suitable for intramuscular injection.

Other immunogens for use in the invention are disclosed in the coassigned U.S. Pat. Nos. 5,023,077, 5,488,494; 5,607,676, 5,866,128; 5,609,870; 5,688,506, and 5,662,702 which are incorporated herein by reference in their entirety.

It has been shown that G17-specific antibodies raised, for example, against the instant G17DT immunogen were affinity-purified from rabbit serum and tested for their ability to inhibit in vitro the binding of radioiodinated human G17 to AR42J cells, a rat pancreatic cancer cell line that expresses gastrin receptors. It was shown that the anti-G17 antibodies, pre-mixed with the labeled G17, significantly (>90%) inhibited the binding of G17 to the cells. This data demonstrate their capacity of the antibodies to neutralize the biological activity of human G17 in pancreatic cancer cells.

G17DT does not cause significant systemic side effects, and no evidence has been found for deleterious effects of long-term neutralization of G17 gastrin and Gly-G17 gastrins. The only significant side effect following immunization-with G17DT is injection site reactions.

Neutralization of the endocrine and autocrine/paracrine effects of G17 and glycine-extended G17 gastrin is proposed as a mechanism by which G17DT immunization can reduce gastrin-stimulated tumor growth, and increase survival of the patient. A G17DT formulation has been developed that elicits an immune response while exhibiting an acceptable local reactogenicity.

Furthermore, as described in the co-assigned international patent application serial number PCT/US99/10750, anti-gastrin immunization treatment combined with lower than normal amounts of Leucovorin/5-FU, has been advantageously effective.

The methods of the invention are directed to the treatment of gastrin hormone-dependent tumors in animals, including humans, and comprise administering to a patient an anti-CCK-B/Gastrin-receptor immunogen, which induces the formation of antibodies in the immunized patient which bind to the CCK-B/gastrin-receptor on the tumor cells. Antibodies bound to the cell receptors block the binding of the hormone to the receptor and thereby inhibit the growth promoting effects of the hormone. More importantly the receptor/anti GRE1 (anti-gastrin receptor epitope 1) antibody complex is rapidly internalized, traverses the cytoplasm and enters the nucleus. The complex one in the nucleus triggers the affected tumor cells to commit suicide (apoptosis).

The immunogens of the invention comprise natural or synthetic peptides of the human CCK-B/gastrin-receptor which act as immunomimics. In particular, two synthetic peptides have been developed as the immunomimics. These peptides, developed from the amino acid sequence of the CCK-B/gastrin-receptor, are immunogenic and cross-reactive with the endogenous CCK-B/gastrin-receptor of tumor cells both in vivo and in vitro. Peptide 1 consists of amino acids 5 through 21 of the CCK-B/gastrin-receptor sequence KLNRSVQGTGPGPGASL (Peptide 1, SEQ ID NO.: 1 in the Sequence Listing). Peptide 1 constitutes part of the amino-terminal domain of the receptor and is located on the extracellular surface of the cell membrane.

In another embodiment, the immunogen comprises Peptide 4, which consists of the amino acid sequence of the CCK-B/gastrin-receptor: GPGAHRALSGAPISF (Peptide 4, SEQ ID NO.: 2 in the Sequence Listing). Peptide 4 is part of the fourth extracellular domain of the receptor and it too is on the outer side of the cell membrane.

The immunogens may also comprise an extension or spacer peptide suitable for projecting the immunomimic peptide away from the protein carrier and to enhance its capacity to bind the lymphocyte receptors. A suitable spacer peptide has the amino acid sequence SSPPPPC (Serine (Ser) spacer, SEQ ID NO.:3 in the Sequence Listing). However, other spacer peptides would be suitable as well. The immunomimic peptides, with or without the spacer, are then conjugated to a protein carrier, such as Diphtheria toxoid, via a cysteine residue at the carboxy terminal end. The spacer peptides are not immunologically related to the CCK-B/gastrin-receptor-derived peptides and should therefore enhance, but not determine, the specific immunogenicity of the receptor-derived peptides.

The presence and density of CCK-B/gastrin-receptors on tumor cells in a patient can be determined in vitro by reacting labeled anti-receptor antibodies with a sample of obtained from a tumor biopsy. The anti-receptor antibodies can be labeled with either a radioactive tracer, a dye, an enzyme or a fluorescent label, as known in the art. In addition, the responsiveness of the tumor cells to gastrin can be evaluated in vitro from a tumor biopsy sample of the patient using standard techniques. Patients having tumor biopsy samples positive for the CCK-B/gastrin-receptor antibody assay are typical candidates for treatment by the methods of the invention.

An effective dosage ranging from 0.001 to 5 mg of the immunogenic composition is administered to the patient for the treatment of the gastrointestinal cancer. The effective dosage of the immunogenic composition should-be capable of eliciting an immune response in a patient consisting of effective levels of antibody titer against the CCK-B/gastrin-receptor 1-3 months after immunization. Following the immunization of a patient, the effectiveness of the immunogens is monitored by standard clinical procedures, such as ultrasound and magnetic resonance imaging (MRI), to detect the presence and size of tumors. The antibody titer levels against the receptor may also be monitored from a sample of blood taken from the patient. Booster immunizations are given as required to maintain an effective antibody titer. Effective treatment of gastrin-dependent cancers, such as stomach, liver, pancreatic and colorectal adenocarcinomas, according to this method should result in inhibition of tumor growth and a decrease in size of the tumor.

The antibodies raised by the anti-CCK-B/gastrin-receptor immunogens of the present invention may have anti-trophic effects against gastrin-dependent tumors by three potential mechanisms: (i) inhibition of gastrin binding to its receptor, (ii) degradation or disruption of the signal transduction pathway of tumor cell proliferation; and (iii) induction of apoptosis (or cell suicide) in cells where receptor/antibody complexes are internalized and migrate into the nucleus.

In another embodiment of the invention, anti-CCK-B/gastrin-receptor antibodies are administered to a patient possessing a CCK-B/gastrin-receptor-responsive tumor. The antibodies specifically bind to the CCK-B/gastrin-receptors on the tumor cells. The binding of the antibodies to the receptors prevents the binding of gastrin to its ligand in the membranes of cells and, therefore, the growth signal for the gastrin-dependent tumor cells is inhibited and the growth of the tumor is arrested. The antibodies are preferably chimeric or humanized antibodies, or fragments thereof, which effectively bind to the target receptor and may be produced by standard techniques, such as, e.g., those disclosed in U.S. Pat. Nos. 5,023,077, 5,468,494, 5,607,676, 5,609,870, 5,688,506 and 5,662,702. These exogenously produced antibodies may also be useful for killing tumor cells that bear the CCK-B/gastrin-receptor on their plasina membranes by virtue of their inhibiting the growth of the tumor cells or delivering a toxic substance to the tumor cell. Therapeutic anti-CCK-B/gastrin antibodies are those reactive with extracellular domains 1 and 4 of the receptor protein as GRE-1 and GRE-4, respectively. The inhibition of tumor growth in this method of immunization is also monitored by ultrasound imaging and MRI and repeated immunizations are administered as required by the patient.

The effectiveness of the antibodies in inhibiting tumor cell growth and killing of tumor cells can be enhanced by conjugating cytotoxic molecules to the anti-CCK-B/gastrin antibodies and the anti-gastrin G17 or G17-gly antibodies. The cytotoxic molecules are toxins, for example, cholera toxin, ricin, α-amanitin, or radioactive molecules labeled, for example, with $^{125}$I or $^{131}$I, or chemotherapeutic agents, as for example, cytosine arabinoside or 5-fluorouridine (5-FU).

In addition to antibodies radiolabeled with $^{125}$I and $^{131}$I, the anti-CCK-B/Gastrin-receptor antibodies can also be labeled with radionuclides such as $^{111}$Indium and $^{90}$Yttrium. In this aspect of the invention, the antibodies are useful for the detection and diagnosing of CCK-B/gastrin-receptor possessing tumors in vivo, by administering these antibodies to the patient, and detecting bound antibodies on CCK-B/gastrin-receptor-containing tumor cells. After allowing the radio labeled anti-CCK-B/gastrin antibodies to reach the tumor, about 1-2 hours after injection, the radioactive, "hot spots" are imaged using standard scintigraphic procedures as previously disclosed (Harrison's Principles of Internal Medicine, Isselbacher et al. eds. 13$^{th}$ Ed. 1994).

The compositions in which the immunogens are administered for the treatment of gastrin-dependent tumors in patients may be in a variety of forms. These include, for example, solid, semi-solid and liquid dosage forms, such as tablets, powders, liquid solutions, suspensions, suppositories, and injectable and infusible solutions. The preferred form depends on the intended mode of administration and therapeutic applications. The compositions comprise the present immunogens and suitable pharmaceutically acceptable components, and may include other medicinal agents, carriers, adjuvants, excipients, etc. Suitable adjuvants may include nor-muramyl dipeptide (nor-MDP, Peninsula Labs., CA), and oils such as Montanide ISA 703 (Seppic, Inc., Paris, France), which can be mixed using standard procedures. Preferably, the compositions are in the form of a unit dose. The amount of active compound administered for immunization or as a medicament at one time, or over a period of time, will depend on the subject being treated, the manner and form of administration, and the judgment of the treating physician.

The anti-CCK-B/gastrin-receptor antibodies of the invention for passive immunization can be administered to a patient intravenously using a pharmaceutically acceptable carrier, such as a saline solution, for example, phosphate-buffered saline.

The pharmacology and toxicology for the instant combined treatment of advanced pancreatic cancer is described below:

Example A

G17DT was administered to 28 patients with advanced pancreatic adenocarcinoma at weeks 0, 1 and 3 at a 250 μg dose [16]. Only one patient failed to mount an antibody response. G17DT was well tolerated with no systemic side effects. One patient developed a sterile abscess that settled following aspiration. Survival was found to be significantly improved in G17DT patients when compared to an historical control matched in terms of age, stage and co-existing morbidity by POSSUM scoring [40].

Concerning the response rates of subjects with pancreatic cancer the median time to onset of the immune response to G17DT appears to be dose related and to be optimal at ≧250 μg G17DT.

Example B

The immuno-electronmicroscopy studies used an antiserum directed against the amino-terminal end of the CCK-B/gastrin-receptor (GRE-1 epitope) show that after one hour incubation, the distribution of immunogold-label CCK-B/gastrin-receptor antibody was quickly internalized as 12% of the antibody receptor complex was associated with the cell membrane, 36.6% within the cytoplasm, 7.9% in the nuclear membrane and, quite surprisingly, 43.5% within the cell nucleus. Areas of intense CCK-B/gastrin-receptor immunoreactivity within the nucleus were found on chromatin, which may suggest specific binding sites for regulation of the DNA.

These electron microscopy studies with anti-immunoglobulin conjugated to gold beads (immunogold) reveal that an extremely rapid turnover of the anti-receptor/receptor complex occurs in the tumor cells; as early as 10 seconds after exposure to antibodies, complexes are detectable in the cell nucleus.

Example C

Immunological Efficacy

Patients' sera were assessed for antibodies to G17 gastrin at 2-4 weekly intervals. Anti-gastrin-17 antibodies were measured using a titration and inhibition radioimmunoassay with $^{125}$I labeled human gastrin-17. Assays for antibodies to G17 gastrin in the pancreatic cancer trials 1 and 2 have been performed by a G17 antigen-based ELISA.

The pharmacodynamics of the immune response to G17DT was evaluated as a function of the dose and treatment regimen for G17DT. The frequency of seroconversion and time to onset of production of G17 gastrin-specific antibodies was used to estimate the optimal dose.

A positive immune response in test serum by RIA was defined as being ≧40 fold above non-specific background determined on a 1:40 dilution of pre-immune subject serum within the first 12 weeks post-immunization. This corresponds to approximately 10% of total $^{125}$I G17 cpm added in the RIA assay. A positive response in the ELISA assay approximates ≧4 units in the ELISA assay which is comparable to that observed by RIA.

To facilitate comparison of doses and formulations, the immune response up to and including the 12-week time point observed in subjects with non-resectable, locally advanced (stage II/III) and metastatic (stage IV) pancreatic cancer were used to determine the proportion of immune responders among the treatment groups in the various studies. The proportion of immune responders and the median time to develop an immune response are summarized in Tables A and B, respectively.

A dose finding phase II study of G17DT in 22 patients with pancreatic carcinoma demonstrated greater survival in patients who mounted an adequate antibody response when compared to non-responders (7.89 versus 4.93 months) [39].

TABLE A

Immune response in subjects with Stage II-IV pancreatic cancer

| Study | | Studies 1&2 (Stage II-IV) | | |
|---|---|---|---|---|
| G17DT Dose | Schedule | n | N$^{a,b}$ | % |
| 10 μg | 0, 4, 8 wk | — | — | — |
| 10 μg | 0, 2, 6 wk | — | — | — |
| 100 μg | 0, 4, 8 wk | — | — | — |
| 100 μg | 0, 2, 6 wk | 5 | 13 | 38 |
| 165 μg | 0, 4, 8 wk | — | — | — |
| 250 μg | 0, 4, 8 wk | — | — | — |
| 250 μg | 0, 2, 6 wk | 6 | 10 | 60 |
| 250 μg | 0, 1, 3 wk | — | — | — |
| 330 μg | 0, 4, 8 wk | — | — | — |
| 330 μg | 0, 2, 6 wk | — | — | — |
| 330 μg | 0, 2, 10 wk | — | — | — |

TABLE A-continued

Immune response in subjects with Stage II-IV pancreatic cancer

| Study | | Studies 1&2 (Stage II-IV) | | |
|---|---|---|---|---|
| G17DT Dose | Schedule | n | N[a,b] | % |
| 495 μg | 0, 4, 8 wk | — | — | — |
| 990 μg | 0, 4, 8 wk | — | — | — |
| Total | | 11 | 23 | 48 | n = number of subjects with an immune response.
N = number of subjects (immune responders and non-responders) that have completed 12 weeks
% = (n/N) × 100
[a]In study 1, 4 subjects have not completed 12 weeks (evaluation ongoing).
[b]In study 2, 11 subjects have not completed 12 weeks (evaluation ongoing); no immune response data available.

TABLE B

Time to immune response in subjects with Stage II-IV pancreatic cancer

| Study G17DT Dose | Schedule | 1[a] & 2[b] (Stage II-IV) Median (weeks) ± SD |
|---|---|---|
| 10 μg | 0, 4, 8 wk | — |
| 10 μg | 0, 2, 6 wk | — |
| 100 μg | 0, 4, 8 wk | — |
| 100 μg | 0, 2, 6 wk | 10 ± 1 |
| 165 μg | 0, 4, 8 wk | — |
| 250 μg | 0, 4, 8 wk | — |
| 250 μg | 0, 2, 6 wk | 6 ± 3 |
| 250 μg | 0, 1, 3 wk | — |
| 330 μg | 0, 4, 8 wk | — |
| 330 μg | 0, 2, 6 wk | — |
| 330 μg | 0, 2, 10 wk | — |
| 495 μg | 0, 4, 8 wk | — |
| 500 μg | 0, 4, 8 wk | |
| 990 μg | 0, 4, 8 wk | — |
| Mean | | 8 ± 2 |

[a]In study 1, 4 subjects have not completed 12 weeks (evaluation ongoing).
[b]In study 2, 11 subjects have not completed 12 weeks (evaluation ongoing); no immune response data available.

Chemotherapy

Example 1

Activity of Gemcitabine

The US FDA approved gemcitabine for use in pancreatic cancer based on the results from several clinical trials [GEMZAR (gemcitabine HCl) package insert, 1996, 1998, summarized in Table 3]. Subjects with locally advanced or metastatic disease were treated with gemcitabine 1000 mg/m$^2$ weekly×7, or ×3, followed by one week of rest, then weekly×3 every four weeks thereafter. Early Phase II trials indicated that a significant number of subjects experienced some palliation of symptoms despite only modest objective response rates. To quantitate these effects, a novel end point termed Clinical Benefit Response was developed for use in subsequent trials.

Clinical Benefit Response is a composite of degrees of pain (analgesic consumption and pain intensity), Karnofsky performance status, and weight change. Gemcitabine was the first agent to be approved using clinical benefit response as an endpoint. Clinical benefit required a sustained (≧4 weeks) improvement in at least one parameter without worsening in any others. Subjects were considered clinical benefit responders only if they showed at least a 50% reduction in the level of pain (Memorial Pain Assessment Card) or consumption of pain medication, or at least a 20-point improvement in performance status (Karnofsky Performance Scale) for a period of at least four consecutive weeks, without showing any sustained worsening in any of the other parameters. A subject was also considered a clinical benefit positive responder if stable in all these parameters.

Example 2

Therapy with Gemcitabine

Prior to the approval of gemcitabine (GEMZAR, Eli Lilly & Co.) in 1996 for the first-line treatment of locally advanced and metastatic adenocarcinoma of the pancreas, 5-fluorouracil (5-FU) had been the standard of GI or pancreatic cancer care for 30 years. A review [50] of 28 Phase II trials involving 25 new agents showed that none provided any improvement over 5-FU in subject outcome, with a median objective response rate of 0% (range 0-14%) and a median survival of 3 months (range 2-8.3 months). Suggestions that combined chemotherapeutic treatments offered improvements over 5-FU alone were not confirmed in randomized Phase III trials [50].

Gemcitabine exhibits several self-potentiation mechanisms which enhance its incorporation into DNA [76]. These effects are mediated via interactions of gemcitabine and its metabolites with the enzymes of pyrimidine nucleotide metabolism and are believed to be significant in producing the high concentration of active drug in cells and in prolonging the half-life of active drug in cells. These include the following:

Gemcitabine triphosphate directly inhibits dCMP deaminase, thus inhibiting the breakdown of gemcitabine monophosphate to difluorodeoxyuridine monophosphate (the major breakdown pathway)

Gemcitabine triphosphate may also inhibit CTP synthase, which catalyzes the synthesis of CTP from UTP and ammonia (or glutamate), additionally depleting dCTP pools.

Inhibition of ribonucleotide reductase by gemcitabine diphosphate reduces the concentrations of dCTP and dCDP, both of which feedback inhibit deoxycytidine kinase. Thus, more gemcitabine is phosphorylated because the feedback inhibition is removed.

Gemcitabine has also been shown to be a potent radiosensitizer. This activity does not parallel the incorporation of the phosphorylated drug into DNA. Rather, it parallels the intracellular depletion of dATP, suggesting that the inhibition of ribonucleotide reductase is the key mechanism of this action [73] [74] [1]. In general, agents (e.g. urea) that reduce dNTP pools act as radiation sensitizers. The intermediate diFdCDP (gemcitabine diphosphate) is a potent inhibitor of ribonucleotide reductase. This inhibition causes a decrease in all four deoxynucleotide triphosphate intracellular pools, which results in an inhibition of DNA synthesis. Variation in the extent of depletion of each dNTP pool in different cell types suggests that the greater depletion of the dATP pool in particular observed in solid tumor cell types may account for the greater clinical activity of gemcitabine in solid tumors [74] [1].

Gemcitabine rapidly distributes into total body water after IV administration. The volume of distribution is affected by duration of infusion, age, and sex. Longer infusions result in higher concentrations.

Clearance is independent of dose and duration of infusion but is variable, and is influenced by age. Because the volume of distribution increases with longer infusion times, its elimination half-life is longer when it is infused over a longer period.

Gemcitabine is deaminated by cytidine deaminase in plasma to difluorodeoxyunridine, which is inactive. Only 5% is excreted unchanged as gemcitabine.

Gemcitabine is generally less well tolerated than 5-FU, but despite a higher incidence of adverse events, its overall toxicity is considered moderate. There is no evidence of cumulative toxicity.

A treatment of the invention combines immunoneutralization of G17 gastrin or G17-Gly gastrin with the chemotherapy with gemcitabine. The advantageous aspect of this combination affords a lower dosage of gemcitabine or irinotecan (or some similarly amenable and approved anti-cancer drug) such that the toxicity and other adverse side effects are reduced. In addition, the immunization with, e.g., G17-DT immunogen containing compositions, can be administered at a time preceding the chemotherapy in order to avoid suppressing of the immuno response before a sufficient titer of auto-antisera has been raised in the treated subject.

Example 3

Therapy with Irinotecan

Irinotecan injection (irinotecan hydrochloride injection) is a semisynthetic derivative of camptothecin, an alkaloid extract from plants such as Camptotheca acuminata. The chemical name is (S)-4,1-diethyl-3,4,12,14-tetrahydro-4-hydroxy-3,14-dioxi-[H-pyrano[3',4':67]-indolizino[1,2-b]quinolin-9-yl-[1,4'-bipiperidine]-1'-carboxylate, monohydrochloride, trihydrate. It is supplied as a sterile, pale yellow, clear, aqueous solution. Each milliliter of solution contains 20 mg irinotecan. (The Camptosar package insert provides detailed labeling information for irinotecan). Irinotecan is an emetogenic. Therefore patients may receive premedication with antiemetic agents. Irinotecan therapy had been shown to cause GI adverse effects, in particular early and late diarrhea. Early diarrhea may be accompanied by cholinergic symptoms. Prophylactic or therapeutic administration of atropine should be considered in patients experiencing cholinergic symptoms. Late diarrhea should be promptly treated with loperamide. In addition to the GI manifestations, irinotecan has been shown to cause myelosuppresion and hypersensitivity reactions. Only patients with adequate hematologic, renal, and hepatic function, as well as patients with no contraindication to irinotecan from previous irinotecan-based therapy, are able to avoid or immunize the frequency and severity of toxic effects such as neutropenia and GI abnormalities.

Patients are permitted to remain on the medications they are taking except for immunosuppressants, including systemic (i.e., oral or injected) corticosteroids. All concomitant medications should be recorded on the appropriate page of the CRF.

Palliative radiotherapy is allowed. In the event that gemcitabine therapy is terminated because of a SAE, G17DT immunization can be continued.

Example 4

Therapy with Cisplatin

Injections with Platinol, a solution of cisplatin or cis-diammine dichloroplatinual II, is used mostly in combination with other cytotoxic agents has used as a potential cure of testicular germ cell neoplasms. Substantial activity has been observed in the treatment of small cell lung cancer, bladder cancer and ovarian germ cell tumors. According to the invention, cisplatin may augment antipancreatic cancer treatment in combination with other pharmaceutically acceptable cytotoxic agents and immunogens or exogenous application of anti-cancertroph antibodies. Suitable effective dosing may range as high as 1000 mg/m$^2$ per week although the chemotherapeutic effect may be enhanced with simultaneous immunotherapy so as to allow lower chemotherapeutic dosages.

Example 5

Effect of Gemcitabine on G17DT Immunogenicity

The example depicts an in vivo test to assess the effect of the chemotherapeutic agent Gemcitabine on the immunogenicity of the G17DT immunogen. For that purpose, as a model animal system, mice were immunized intraperitoncally (IP) with 125, 250 and 500 µg doses of G17DT in Montanide ISA 703 emulsions of 0.1 ml volume on days 0, 28 and 56. Gemcitabine was given intravenously (IV) at a dose of 21.4 mg/kg in a volume of 0.2 ml on days 0, 7, 14, 21, 28, 35, 42, 56, 63 and 70. Control mice received saline vehicle without the chemotherapeutics. The resultant anti-G17 antibody responses were measured by ELISA in sera collected every two weeks, and one bleed at day 21, over the course of the study.

The G17DT immunogen was formulated under sterile conditions using PBS (physiological saline solution) as diluent. The emulsion was produced by mixing the agueous phases of immunogens with Montanide ISA 703 at an oil: aqueous phase w/w ratio of 70:30.

Aliquots 8-10 mg dry Gemcitabine were weighed to be solubilized in PBS at a human treatment concentration of 3.424 mg/ml Gemcitabine before i.v. administration.

The results of the treatment over the course of 84 days showed that all mice responded to G17DT immunogen with similar kinetics comparing the median responses of all groups. (see Table 1).

Mice immunized with 125 µg G17DT manifested a statistical decrease in mean anti-G17 titers when concomitantly treated with Gemcitabine. However, the suppression was overcome by increasing the dose of immunogen to 250 µg or 500 µg G17DT.

This second part of the example depicts cell proliferation of human pancreatic cell lines, PANC-1, BxPC3 and PAN-1 using a tetrazolium-based combined with anti-gastrin G17 antibodies induced by G17DT (10-500 µg/ml). The G17DT elicited antibodies are active against both serum-associated and tumor-secreted, proliferative forms of gastrin. The PAN-1 cell were administered at clinically reflective doses.

G17DT concentrations of 100 and 50 µg/ml increased the in vitro inhibitory effects of Gemcitabine (1.0-0.01 µg/ml) by 11-38% (p<0.05, ANOVA) when compared to the individual agents for all three cell lines.

In vivo G17DT alone inhibited basal pancreatic tumor weight by 33% (p=0.016, ANOVA) compared to 38% for Gemcitabine (p=0.004, ANOVA). When combined the agents inhibited tumor weight by 55% which was significant from G17DT alone (p=0.025). Thus the immunological agent G17DT may promote the therapeutic efficacy of Gemcitabine.

TABLE 1

Mean Anti-G17 Titer ± Standard Error Plus Student's t-Test

| | DAY OF STUDY | | | | | | | |
|---|---|---|---|---|---|---|---|---|
| | 0 | 14 | 21 | 28 | 42 | 56 | 70 | 84 |
| Group 1; 125 µg G17DT Placebo Treatment | 0 | 1,006 ± 240 | 1,132 ± 140 | 1,227 ± 210 | 74,780 ± 7,655 | 40,200 ± 4,883 | 241,140 ± 37,905 | 95,940 ± 23,248 |
| Group 2; 125 µg G17DT Gemcitabine Treatment | 0 | 292 ± 59 | 408 ± 77 | 408 ± 104 | 43,860 ± 11,118 | 21,497 ± 6,813 | 64,200 ± 18,788 | 37,774 ± 9,480 |
| t-test Group 1 vs. 2 P(T <= t) two-tail | | 0.020[1] | 0.002[1] | 0.008[1] | 0.051[1] | 0.054[1] | 0.003[1] | 0.049[1] |
| Group 3; 250 µg G17DT Placebo Treatment | 0 | 2,047 ± 717 | 2,074 ± 575 | 2,349 ± 622 | 86,840 ± 34,076 | 25,913 ± 8,730 | 71,788 ± 21,755 | 42,166 ± 13,013 |
| Group 4; 250 µg G17DT Placebo Treatment | 0 | 923 ± 242 | 1,899 ± 724 | 2,863 ± 1,284 | 169,300 ± 65,955 | 40,620 ± 11,494 | 256,560 ± 59,743 | 73,220 ± 17,674 |
| t-test Group 3 vs. 4 P(T <= t) two-tail | | 0.176 | 0.855 | 0.728 | 0.299 | 0.338 | 0.020[1] | 0.195 |
| Group 5; 500 µg G17DT Placebo Treatment | 0 | 1,555 ± 160 | 4,703 ± 963 | 6,489 ± 1,545 | 107,398 ± 26,096 | 43,146 ± 13,699 | 196,000 ± 44,006 | 118,667 ± 50,824 |
| Group 6; 500 µg G17DT Placebo Treatment | 0 | 1,100 ± 452 | 1,715 ± 790 | 4,372 ± 2,127 | 653,925 ± 360,669 | 162,900 ± 90,679 | 166,800 ± 87,853 | 77,450 ± 13,846 |
| t-test Group 5 vs. 6 P(T <= t) two-tail | | 0.370 | 0.043[1] | 0.436 | 0.130 | 0.184 | 0.760 | 0.407 |

[1]Statistical significance at $p \leq 0.05$

Another embodiment of the present invention provides treatment with more than one chemotherapeutic agent in combination with active immunization against an appropriate growth factor and/or growth factor receptor. For example, such treatment can involve a combination of 5-FU/Leucovorin or 5-FU plus cisplatinum.

As a preclinical experiment, mice were treated with a combination of the two anticancer agents 5-FU and Cisplatinum and tested as to the extent of numerous suppressive effects.

Example 6

Effect of 5-FU & Cisplatinum on G17DT Immunogenicity

This example concerns the effect of co-treatment with the chemotherapeutic agent 5-fluorouracil (5-FU) and Cisplatinum (II)— Diamine Dichloride (Cisplatinum as the active ingredient of the drug formulation cisplatin) upon the immunogenicity of G17DT immunogen in mice.

G17DT immunogen was formulated with MONTANIDE ISA 703 at 1.25 mg/ml of G17DT conjugate. Mice were immunized intraperitoneally (IP) with an injection volume of 0.1 ml delivering a dose of 125 µg G17DT on days 0, 28 and 56. The chemotherapeutic dosing regimen was based on the doses recommended for human patients. Thus the combined 5-FU plus Cisplatinum was administered to the test group on day 0, following by 5-FU above on days 1 and 2 by intravenous injection in 0.2 ml volume at doses of 10.0 mg/kg 5-FU and 1.0 mg/kg Cisplatinum. Control mice were immunized while receiving saline vehicle without the chemotherapeutics. As supportive therapy for the potential dehydration caused by Cisplatinum, all mice received IP 1.0 ml PSS (Physiological Saline solution). The anti-G17 antibody levels in sera collected at 14-day intervals (plus an additional on d 21) were assayed by ELISA.

The G17 DT immunogen was formulated as described in Example 4. The 5-FU and Cisplatinum formulations were prepared at 10.0 mg/kg for 5-FU and 1.0 mg/kg for Cisplatinum to provide calculated doses of 320 mg of 5-FU and 32 mg of Cisplatinum. The dry aliquots of 5-FU and Cisplatinum were reconstituted on treatment days by dissolution in the same PSS to yield 1.6 mg/ml and 0.16 mg/ml, respectively. For day 1 and 2, 5-FU alone was given at 1.6 mg/ml in PSS.

The subject mice were ten CAPF1 female, about 18 months old. All mice were G17-immunized at a dose (IP) of 0.1 ml of G17 DT on days 0, 28, 56 of study. All chemotherapeutics were administered in volumes of 0.2 ml. Control mice received 0.2 ml of PSS placebo, according to the treatment regimen. To counter Cisplatinum related dehydration, all mice were injected IP with 10 ml PSS per mouse. The mice were bled every 14 days starting on day 0 and ending on day 84. The sera were assayed by ELISA, showing that all mice responded to G17 DT immunogen with significant titers of anti-G17 antibodies. The responses of both groups peaked on day 70. The mean/median response of the combination treatment group was overcome by the administration of the second injection of immunogen. The results indicate that the 5-FU plus Cisplatinum treatment (following a dose regimen designed for humans) had no statistically significant negative effect on the anti-G17 antibody response.

The treatment(s) can be administered up to disease progression, unacceptable toxicities or withdrawal of consent. If the unacceptable toxicities are due to chemotherapy and the subject's disease has not progressed, chemotherapy can be stopped and immunotherapy can be continued as planned. Immunotherapy is continued after the onset of disease progression and is stopped only for unacceptable toxicity attributable to G17DT or withdrawal of consent.

TABLE 2

A Comparison of Anti-G17 Antibody Mean Titers by ELISA (Ex. 6) (plus/minus S.D.)

| | DAY OF STUDY | | | | | | | |
|---|---|---|---|---|---|---|---|---|
| | 0 | 14 | 21 | 28 | 42 | 56 | 70 | 84 |
| Group 1, 125 µg | 100 | 997 ± 194 | 1.099 ± 249 | 1.029 ± 355 | 70.660 ± 30.571 | 48.020 ± 22382 | 108300 ± 44771 | 50500 ± 11449 |
| Group 2, 125 µg G17DT, 5-FU-CISPLATINUM Treatment | 100 | 874 ± 222 | 739 ± 265 | 266 ± 83 | 81.400 ± 34429 | 35.966 ± 14014 | 15.4360 ± 41771 | 48.860 ± 10797 |
| t-test Group 1 vs. 2 $P(T <= t)$ two-tail | | 0.687 | 0.351 | 0.066 | 0.821 | 0.660 | 0.473 | 0.920 |

Example 7

A. Combined Treatment with Immunization and Gemcitabine (Protocol)

The following clinical treatment regime is provided:

| MEDICATION | G17DT | Gemcitabine |
|---|---|---|
| (immunotherapy + chemotherapy) | Days 1, 28, 56 | Day 1 and continue once a week for a total of 7 weeks, followed by 1 week rest. Then continue with 4-week cycles of 3 weekly administrations, followed by 1 week rest each cycle. |

Sampling Schedules:

| Blood Chemistry: | weekly |
|---|---|
| Hematology: | weekly |
| Urinalysis: | weekly |
| Immunology: | bi-weekly to week 12, monthly after week 12 |

Diagnostics Prior to Entry:

| Endoscopy: | pre-enrollment |
|---|---|
| CT scan and Chest x-ray: | pre-enrollment |

Diagnostics Follow Up:

| CT scan: | monthly |
|---|---|
| Chest x-ray: | as needed |

Gemcitabine

| Dose: | 1000 mg/m² |
|---|---|
| Route: | in 250 ml of 0.9% sodium chloride over 30 min., IV infusion |
| Schedule: | Day 1 and continue once a week for a total of 7 weeks, followed by 1 week rest. Then continue with 4-week cycles of 3 weekly administrations, followed by 1 week rest each cycle. |

Alternatively, the dosage of gemcitabine may be reduced to about 750 mg/m² or 500 mg/m² or less.

B. Combination with Irinotecan

Irinotecan was initially approved as second-line therapy for patients with metastatic colorectal carcinoma whose disease has recurred or progressed following 5-FU-based therapy. Subsequently, irinotecan in combination with 5-FU and LV was approved as first-line therapy for treatment of this disease. Irinotecan-based therapy, however, is not without significant morbidity, including diarrhea and myelosuppression. To reduce these side effects, dose adjustments are often necessary that may reduce the efficacy of irinotecan. Patients who fail irinotecan-based therapy, thereby, are left with few options for the efficacious treatment of their disease.

Immunotherapy combined with irinotecan has the potential to enhance overall therapeutic effect, while reducing side effects associated with irinotecan treatment. In addition to having antitumor activity on its own, gastrin neutralization by G17DT administered prior to 5-FU and LV treatment has been shown to enhance the antitumor activity of 5-FU and LV therapy, and potentiated the activity of suboptimal doses of 5-FU on rat colorectal tumors.

Using this rationale, it can be proposed that G17DT may also potentiate the efficacy of irinotecan and offer a potentially new treatment modality that combines the cytostatic action of antigastrin immunization with the cytotoxic effects of chemotherapy. In addition, immunization with G17DT could be used with drugs whose maximum doses must be reduced due to associated serious AEs.

G17DT is administered as an intramuscular injection of 250 µg in 0.2 ml, vehicle. To elicit an immune response, G17DT is administered in the initial treatment period at Week 1. In the absence of Grade 2 or greater allergic reaction to G17DT following first injection of G17DT, additional doses of G17DT are administered at Weeks 5, 9; thereafter G17DT is administered following a decrease in anti-G17 titer of 50% or more from the maximum titer.

Irinotecan is administered as an intravenous infusion of 125 mg/m$^2$ over 90 minutes starting at Week 5 or 4 weeks after the initial administration of G17DT. Each cycle of treatment consists of irinotecan i.v. administration by infusion once weekly for 4 weeks, followed by a 2-week rest period. Additional cycles of treatment are repeated until disease progression, dose limiting toxicity (DLT), or patient withdrawal. If necessary, doses of irinotecan can be adjusted by using specific dose modification rules to accommodate individual patient tolerance of treatment. In the absence of DLT or progressive disease, patients continue the G17DT-irinotecan combination treatment regimen. This dosing regimen is based on results from 3 open-label, single-agent clinical studies involving a total of 304 patients.

Example 7

Tumor Response Criteria

Abdominal/pelvic CT scan with IV contrast and chest x-ray (as needed) can be used to assess tumor burden.

Examples of such lesions evaluated by clinical examination or imaging tools include:
a skin nodule or superficial lymph node minimum≧10 mm×≧10 mm
a liver lesion, soft tissue, lymph node and masses investigated by CT scan (minimum≧20 mm×≧10 mm).

These include all the lesions that can be measured with only one diameter ≧20 mm on CT scan or ≧10 mm on physical examination.

An example of these lesions is a palpable abdominal mass or soft tissue mass that can be measured only in one diameter.

Example 8

Evaluation of Response

Subjects must have received 3 immunizations with G17DT and/or GRE1DT and a minimum of one 7-week cycle or two 4-week cycles of treatment with gemcitabine with at least one follow-up tumor assessment using the same method as baseline to be considered evaluable for response unless "early progression" occurs, in which case they are considered evaluable (in progressive disease). Subjects on therapy for at least this period have their-response classified according to the definitions set out below.

Immune response assessments is made by ELISA on blood samples collected from subjects every 2 weeks up to 12 weeks and every 4 weeks thereafter. Tumor assessment for all lesions must be performed every 4 weeks on therapy until the documentation of the progression. Tumor-response should be reported on follow-up visits every 4 weeks for the subject who goes off study for reason other than progressive disease (PD).

No further anti-tumor therapy is given after end of treatment until disease progression is documented, except if the subject requests further therapy or the investigator deems it necessary. All uni- or bi-dimensionally measurable lesions should be measured every subsequent 4 weeks. Additional assessments should be performed to confirm a response at least 28 days after the first response has been observed. In addition, extra assessments may be performed if there is a clinical suspicion of progression. When multiple lesions are present, this may not be possible and, under such circumstances, up to 6 measurable target lesions which are representative of all organs involved should be selected for the involved sites, giving the priority to bi-dimensionally measurable lesions, then uni-dimensionally measurable lesions.

Best overall response is the best response designation recorded from the start of treatment until disease progression.

Complete and partial responses have to be confirmed by two evaluations of the disease, taken at least 4 weeks apart (see above for assessment time).

No change is only accepted if it is measured at least 4 weeks after the treatment start.

Tumor response, time to progression, time to treatment failure and survival can be analyzed both on an intent-to-treat basis and on the evaluable population.

The period for complete response lasts from the date the complete response was achieved to the date thereafter on which progressive disease is first noted. In those subjects who achieved partial response, only the period of overall response should be recorded. The period of overall response lasts from the day of the first observation of response (partial or complete) to the date of first observation of progressive disease.

Time to disease progression is the time measured from the start of treatment to the first progression, death, or discontinuation of both chemotherapy and immunotherapy, whichever occurs first. Subjects that have not progressed at the time of the final analysis can be censored at the date of their last tumor assessment. Subjects who receive non-study anti-tumor therapy before disease progression can be censored at the date of the last assessment before therapy.

Time to treatment failure is the time measured from the start of treatment to the date of failure (progression, relapse, death or any other cause of treatment discontinuation).

Survival is measured from the start of treatment to the date of death from whatever cause. Subjects alive as of the final analysis will be censored at their last contact date.

The pharmacodynamics of the immune response following the primary series of three injections are assessed by the proportion of immune responders with ≧4 ELISA units sustained for 2 consecutive bleeds in study Arm A attained by week 12 following the first immunization and by the mean and median peak titers. Immunoassays are performed by G17 antigen-based ELISA. The quality of the antibody response is measured by inhibition RIA and assessed by dissociation constant (Kd) and antigen binding capacity (ABC), and ABC/Kd ratio.

The mean and median duration of the immune response from peak titer to <25% of peak titer is assayed in order to determine the time to administer a booster immunization.

Taxanes

Recent treatments of advance prostate cancer include the administration of chemotherapeutic agents such as taxanes. Taxanes, such as, for example, docetaxel, are effective microtubule inhibitors thereby interfering in the further transition of the cell cycle at G2/M check-point. Taxanes have now emerged as a promising class of newly approved chemotherapies currently under investigation in hormone-refractory prostate cancer. A number of recent studies indicate that the taxane, i.e. docetaxel, is particularly active. For example, 35 patients with hormone-refractory prostate cancer were treated with docetaxel at 75 mg/m$^2$ every 21 days while being maintained on androgen suppression. Toxicity remained tolerable throughout the treatment; although there were two deaths during the study, one due to lung toxicity/pneumonia and one due to pulmonary embolus. Responses, defined as a more than 40% PSA decline and a more than 50% reduction of bi-dimensional cross-products in patients with measurable disease, were seen in 17 of the 35 patients enrolled, including one complete response. Responses were maintained for a median of nine months (range, 2 to 24 months). The median overall survival in this study was 27 months. Preclinical studies suggested a potential benefit for the combination of docetaxel with estramustine in the treatment of patients with hormone-refractory prostate cancer. Based on data from two phase I studies, the docetaxel dose applied for phase II study which was undertaken in combination with estramustine in human subjects was 70 mg/m² or 60 mg/m². Phase II studies of docetaxel plus estramustine have demonstrated more than 50% PSA declines in 59% to 88% of patients. Although reduction of the dose of estramustine appears to result in a somewhat lower response rate, the contribution of estramustine to the efficacy of the docetaxel-estramustine combination was not conclusive.

Passive Immunization:

The chemotherapies described above can be combined with passive immunization against cancer growth promoting factors and receptors comprises administration of purified antibodies which can be polyclonal or monoclonal. Monoclonal antibodies are conventionally prepared for treatment in humanized or chimeric form.

The transgenic mouse isolated human antibodies can be further modified by radiolabel or other toxic materials so as to induce necrosis or apoptosis in the target cancer cells. For example, the antibodies, modified or not, will be directed to bind to receptors, many of which will internalize the ab-receptor complex to the nucleus of the cell so as to lead to the affected cell's death, which process may be similar or like apoptosis. Pancreatic carcinoma treatment can include one or more of the combinations of chemotherapeutic agents and active or passive immunotherapies, as described above. However, the treatment are not in any way limited to the specific aforementioned samples. On the contrary, the thrust of the invention suggests a useful variety of combined chemical and immunological agents to slow or decrease tumor growth.

Polyclonal antibodies can be obtained from immunized human and other mammalian sources. One manner of inducing high affinity specific antisera utilizes the immunogen as described above where the antigenic varieties are conjugated to immunogenic carrier. The highly active antibody fractions are isolated and purified by conventional means for inoculation in the cancer patient in need of this treatment. Since this type of passive immunotherapy can utilize the patient's own antibodies, the risk of rejection and other complications can be minimized or entirely avoided.

Treatment with modified, such as radioactive-labeled antibodies is from anti-CCKB/gastrin receptor antibodies would effect cell death by internalized specific irradiation. Furthermore, the combination therapy using gastrin and gastrin receptor immunogens can be administered to immunize or prevent metastasis of gastrin-dependent adenocarcinoma cells. Such metastatic cancer cells may derive from gastric, prostate, pancreatic, or colorectal lesions and localize in other tissues, such as bone, liver, or lymph nodes. Anti-gastrin immunization has been shown to inhibit liver metastasis.

REFERENCES

1. Lawrence, T. S., E. Y. Chang, et al., *Radiosensitization of pancreatic cancer cells by 2',2'-Difluoro-2'-Deoxycytidine.* Int. J. Radiation Oncology Biol. Phys., 1996. 34(4): p. 867-872.
2. Burris III, H. A., M. J. Moore, et al., *Improvements in survival and clinical benefit with gemcitabine as first-line therapy for patients with advanced pancreas cancer: a randomized trial.* Journal of Clinical Oncology, 1997. 15(6): p. 2403-2413.
3. Rehfeld, J. F., L. Bardram, et al., *Cell-specific processing of pro-cholecystokinin and pro-gastrin.* Biochimie, 1988. 70: p. 25-31.
4. Caplin M. et al. *Expression and processing of gastrin in pancreatic adenocaracinoma.* Brit. J. Surgery 2000, 87:1035-1040.
5. Landis, S. H., T. Murray, et al., *Cancer Statistics,* 1998. Ca Cancer J Clin, 1998. 48: p. 6-29.
6. Watson, S. A., L. G. Durrant, et al., *The in vitro growth response of primary human colorectal and gastric cancer cells to gastrin.* Int. J. Cancer, 1989. 43: p. 692-696.
7. Ochiai, A., W. Yasui, et al., *Growth-promoting effect of gastrin on human gastric carcinoma cell line TMK-1.* Japan J. Can. Res., 1985. 76: p. 1064-1071.
8. McRae, L. J., P. A. Kiener, et al., *Role of gastrin and gastrin receptors in the growth of human colon carcinoma cells.* J. Cell Biol., 1986. 103: p. 22a.
9. Kobori, O., M. T. Vuillot, et al., *Growth response of rat stomach cancer cells to gastro-entero-pancreatic hormones.* Int. J. Cancer, 1982. 30: p. 65-67.
10. Ohkura, H., K. Hanafusa, et al., *Gastrin-enhanced tumor growth of a xenotransplan table human gastric carcinoma in nude mice.* Jpn. J. Clin. Oncol., 1980. 10(2): p. 255-263.
11. Smith, J. P., A. P. Fantaskey, et al., *Identification of gastrin as a growth peptide in human pancreatic cancer.* American Journal of Physiology, 1995. 37: p. R135-R141.
12. Douziech, N., A. Lajas, et al., *Growth effects of regulatory peptides and intracellular signaling routes in human pancreatic cancer cell lines.* Endocrine, 1998. 9: p. 171-183.
13. Watson, S. A., G. Robinson, et al., *Detection of gastrin receptors on gastrointestinal tumours using the anti-gastrin receptor monoclonal antibody, 2CL.* Gut, 1993. 4: p. F271.
14. Hoosein, N. M., P. A. Kiener, et al., *Evidence for autocrine growth stimulation of cultured colon tumor cells by a gastrin/cholecystokinin-like peptide.* Experimental Cell Research, 1990. 186: p. 15-21.
15. Smith, A. M., S. A. Watson, et al., *Gastrin may have an autocrine/paracrine role in Barrett's oesophagus and oesophageal adenocarcinoma.* Br. J. Surgery, 1996. 84: p. 706.
16. Seva, C., C. J. Dickinson, et al., *Growth-promoting effects of glycine-extended progastrin.* Science, 1994. 265: p. 410-412.
17. Negre, F., P. Fagot-Revurat, et al., *Autocrine stimulation of AR4-2J rat pancreatic tumour cell growth by glycine-extended gastrin* Int. J. Cancer, 1996. 66(5): p. 653-658.
18. Kopin, A. S., Y. M. Lee, et al., *Expression cloning and characterization of the canine parietal cell gastrin receptor.* Proc. Nat. Acad. Sci., 1992. 89: p. 3605-3609.
19. Marino, L. R., T. Takeuchi, et al., *Expression and post-translational processing of gastrin in heterologous endocrine cells.* The Journal of Biological Chemistry, 1991. 266(10): p. 6133-6136.
20. Finley, G. G., R. A. Koski, et al., *Expression of the gastrin gene in the normal human colon and colorectal adenocarcinoma.* Cancer Research, 1993. 53: p. 2919-2926.
21. Van Solinge, W. W., V. C. Nielsen, et al., *Expression but incomplete maturation of progastrin in colorectal carcinomas.* Gastroenterology, 1993. 104(4): p. 1099-1107.
22. Wank, S. A. f., J. R. Pisegna, et al., *Cholecystokinin receptor family. Molecular cloning, structure, and functional expression in rat, guinea pig, and human.* Ann. N.Y. Acad. Sci., 1994. 713: p. 49-66.

23. Weinberg, D. S., B. Ruggeri, et al., *Cholecystokinin A and B receptors are differentially expressed in normal pancreas and pancreatic adenocarcinoma*. Journal Clin. Invest., 1997. 100(3): p. 597-603.
24. DeWeerth, A., T. Von Schrenck, et al., *Human pancreatic cancer cell lines express the CCKB/gastrin receptor*. Gastroenterology, 1994. A289.
25. Mandair, K. K., P. Towner, et al., *cholecystokinin receptors in human pancreatic cancer cell lines*. eur. J. Cancer, 1998.34: p. 1455-1459.
26. de Weerth, A., T. von Schrenck, et al., *Human pancreatic cancer cell lines express the CCKB receptor*. Hepatogastroenterology, 1999. 46: p. 472-478.
27. Kaufmann, R., H. Schafberg, et al., *Cholecystokinin B-type receptor signaling is involved in human pancreatic cancer cell growth*. Neuropeptides, 1997. 31(6): p. 573-583.
28. Tang, C., I. Biemond, et al., *Expression of receptors for gut peptides in human pancreatic adenocarcinoma and tumour-free pancreas*. British Journal of Cancer, 1997. 75(10): p. 1467-1473.
29. Robertson, J. F., S. A. Watson, et al., *Effect of gastrointestinal hormones and synthetic analogues on the growth of pancreatic cancer*. Int. J. Cancer, 1995. 63: p. 69-74.
30. MacKenzie, J. F. I., C. A. Dovian, et al., *Development of a radioligand binding assay to characterise gastrin receptors in the human gastrointestinal tract*. Gut, 1996. 38: p. A37.
31. Tarasova, N. I., S. A. Wank, et al., *Endocytosis of gastrin in cancer cells expressing gastrin/CCK-B receptor*. Cell Tissue. Res., 1997. 287: p. 325-333.
32. Dethloff, L. A., B. M. Barr, et al., *Inhibition of gastrin-stimulated cell proliferalion by the CCK-B/gastrin receptor ligand CL-988*. Food. Chem. Toxicol., 1999. 37: p. 105-110.
33. Watson, S. A. and R. J. Steele, *Gastrin receptors in gastrointestinal tumors*. 1993: R. G. Landes Company. 95.
34. Watson, S. A., L. G. Durrant, et al., *Growth-promoting action of gastrin on human colonic and gastric tumour cells cultured in vitro*. Br. J. Surg., 1988. 75: p. 342-345.
35. McWilliams, D. F., S. A. Watson, et al., *Coexpression of gastrin and gastrin receptors (CCK-B and CCK-B) in gastrointestinal tumour cell lines*. Gut, 1998. 42: p. 795-798.
36. Kochman, M. L., J. DelValle, et al., *Post-translational processing of gastrin in neoplastic human colonic tissues*. Biochemical and Biophysical Research Communications, 1992. 189(2): p. 1165-1169.
37. Nemeth, J., B. Taylor, et al., *Identification of progastrin derived peptides in colorectal carcinoma extracts*. Gut, 1993. 34(1): p. 90-95.
38. Frucht, H., A. F. Gazdar, et al., *Characterization of functional receptors for gastrointestinal hormones on human colon cancer cells*. Cancer Research, 1992. 52(5): p. 1114-1122.
39. Hoosein, N. M., P. A. Kiener, et al., *Antiproliferative effects of gastrin receptor antagonists and antibodies to gastrin on human colon carcinoma cell lines*. Cancer Research, 1988. 48: p. 7179-7183.
40. Smith, J. P., M. F. Verderame, et al., *Antisense oligonucleotides to gastrin inhibit growth of human pancreatic cancer*. Cancer Lett., 1999. 135: p. 107-112.
40a. Dockray, G. J., A. Varro, et al., *Gastric endocrine cells: gene expression, processing, and targeting of active products*. Physiological Review, 1996. 76(3): p. 767-798.
41. Delvalle, J., K. Sugano, et al., *Progastrin and its glycine-extended posttranslational processing intermediates in human gastrointestinal tissues*. Gastroenterology, 1987. 92: p. 1908-1912.
41a. Iwase, K., M. B. Evers, et al., *Regulation of growth of human gastric cancer by gastrin and glycine-extendedprogastrin*. Gastroenterology, 1997. 113: p. 782-790.
42. Bold, R. J., J. Ishizuka, et al., *Gastrin stimulates growth of human colon cancer cells via a receptor other that CCK-A or CCK-B*. Biochemical and Biophysical Research Communications, 1994. 202(3): p. 1222-1226.
43. Okada, N., A. Kubota, et al., *Evaluation of cholecystokinin, gastrin, CCK-A receptor and CCK-B/gastrin receptor gene expressions in gastric cancer*. Cancer Letters, 1996. 106(2): p. 257-262.
43. Koh, T. J., P. J. Nicholls, et al., *Glycine-extended gastrin promotes growth of a human hepatoma cell line*. Gastroenterology, 1996. 110(4): p. A1089.
44. Stepan, V., M. Sawada, et al., *Glycine-extended gastrin exerts growth-promoting effects on colon cancer cell lines*. Gastroenterology, 1996. 110(4): p. A 1122.
44a. Caplin, M. E., C. Millson, et al., *Serum gastrin levels and identification of CCK-B/gastrin receptor following partial hepatectomy for liver tumours in man*. Gastroenterology, 1996. 110(4): p. A1162.
45. Song, I., D. R. Brown, et al., *The human gastrin/cholecystokinin type B receptor gene: alternative splice donor site in exon 4 generates two variant mRNAs*. Proc. Nat. Acad. Sci., 1993. 90(19): p. 9085-9089.
46. Singh, P., Z. Xu, et al., *Incomplete processing of progastrin expressed by human colon cancer cells: roles of non-carboxyamidated gastrins*. The American Physiological Society, 1994: p. G459-G468.
47. Watson, S. A., Smith, H. M., Michaeli, D., Grimes, S., Caplin, M., Hardcastle, J. D., *Antibodies targeting the aminoterminal portion of the human CCK-B/gastrin receptor inhibit the lives invasion of a human colonic tumor*. Gastroenterology, 1998. 114(4): G2899.
48. Huang, P., S. Chubb, et al., *Termination of DNA synthesis by 9-B-D-Arabinofuranosyl-2-fluoroadenine*. Journal of Biological Chemistry, 1990. 265(27): p. 16617-16625.
49. Li, Y., B. Singh, et al., *Induction of growth inhibition and apoptosis in pancreatic cancer cells by auristatin-PE and gemcitabine*. J. Mol. Med., 1999. 3: p. 647-653.
50. Rothenberg, M. L., M. J. Moore, et al., *A phase II trial of gemcitabine in patients with 5-FU-refractory pancreas cancer*. Annals of Oncology, 1996. 7: p. 347-353.
51. Miyake, A., *A truncated isoform of human CCK-B/gastrin receptor generated by alternative usage of a novel exon*. Biochem. Biophys. Commun., 1995. 208(1): p. 230-237.
52. Biagini, P., G. Monges, et al., *The human gastrin/cholecystokinin receptors: Type B and Type C expression in colonic tumours and cell lines*. Life Sciences, 1997. 61 (10): p. 1009-1018.
53. Upp. J. R., P. Singh, C. M. Townsend, Jr. et al., *Animal significance of gastrin receptors in human colon cancer*. Cancer Res. P. 989, 49(2): p. 488-492.
54. Soll, A. H., Amiran, L. P., Thomas, T., Reedy, T. J., Elashoff, J. D. *Gastrin-receptors on isolated canine parietal cells*. J. Clin. Invet. 1984; 73:1434-1447.
55. Wank, S. A., Pisegna, J. R., de Weerth, A. *Brain and gastrointestinal cholecystokinin receptor family: structure and functional expression*. Proc. Nat. Acad. Sci. USA 1992; 89:8691-8695.

57. Fourmy, D., Zahidi, A., Pradayrol, I., Vay ssette, J., Ribet, A. *Relationship of CCK/gastrin-receptor binding to amylase release in dog.* Pancreatic Acini. Regul. Pept. 1984; 10:57-68.
58. Grider, J. R., Malchlouf, G. M. *Distinct receptors for cholecystokinin and gastrin on muscle cells of stomach and gallbladder.* Am. J. Physiol. 1990; 259: G184-G190.
59. Singh, P., Townsend, Jr. C. M., Thompson, J. C., Narayan, S., Guo, Y. S. *Hormones in colon cancer: past and prospective studies.* Cancer J. 1990; 3:28-33.
60. Scemma, J. L., Fourmy, A., Zahidi, L., Praydayrol, L., Susini, C., Ribet, A. *Characterization of gastrin-receptors on a rat pancreatic acinar cell line (AR4-2J). A possible model for studying gastrin mediated cell growth and proliferation.* Gut 1987; 28:233-236.
61. Wank, S. A. *Cholecystokinin receptors (editorial).* Am. J. Physiol. 1995; 269: G628-G646.
62. Rehfeld, J. F., Bardram, L., Hilsted, L. *Gastrin in human bronchogenic carcinomas: constant expression but variable processing of prograstrin.* Cancer Res. 1989; 49:2840-2843.
63. Ullrich, A., Schlessinger, J. Signal. *Transduction by receptors with tyrosine kinase activity.* Cell 1990; 61:203-212.
64. Todisco, A., Takeuchi, Y., Seva, C., Dickinson, C. J., Yamada, T. *Gastrin and glycine extended progastrin processing intermediates induce different programs of early gene activation.* J. Biol. Chem. 1995; 279:28337-28341.
65. Taniguchi, T., Matsui, T., Ito, M., Marayama, T., Tsukamota, T., Katakami, Y., Chiba, T., Chihara, K. *Cholecystokinin-B/gastrin-receptor signaling pathway involve styrosine phosphorylatins of p125FAK and p42MAP.* Oncogene 1994; 9:861-867.
66. Isselbacher et al. *Harrison's Principles of Internal Medicine, Eds.* 13th Ed. Pages 1690-1691, 1994.
67. Watson, S. A., Durrant, L. G., Elston, P., and Morris, D. L. *Inhibitory effects of the gastrin-receptor antagonist (L-365, 260) on gastrointestinal tumor cells* Cancer, 1991. 68(6); p. 1255-1260.
68. Bock, M. G., DiPardio, R. M., Evans, B. E., Rittle, K. E., Whitter, A., Veber, D, Anderson, E., and Freidinger, A. *Benzodiazepine, gastrin and brain cholecystokinin receptor ligands: L-365,260.* J. Med. Chem., 1989, 32: 13-17.
69. Hughes, J., Boden, P., Costall, B., Domeney, A., Kelly, E., Horwell, D. C., Hunter, J. C., Pinnock, R. D., and Woodruff, G. N. *Development of a class of selective cholecystokinin type B receptor antagonists having potent anxiolytic activity.* Proc. Natl. Acad. Sci., 87: 6728-6732, 1990.
70. Romani, R., Howes, L. G., and Morris, D. L. *Potent new family of gastrin-receptor antagonists (GRAs) produces in vitro and in vivo inhibition of human colorectal cancer cell lines.* Procs. AACR, 35: 397 (Abstract), 1994.
71. Yuki H. et al. *YM022, a potent and selective gastrin/CCK-B receptor antagonist, inhibits peptone meal-induced gastric acid secretion in Heidon hair pouch dogs.* Dig. Dis. Sci. 1997 April 42 (4): 707-714.
72. Takinami Y. et al. *YF476 is a new potent and selective gastrin/cholecystokinin-B receptor antagonist in vitro and in vivo,* Aliment. Pharmacol. Ther. 1997 Feb., 11 (1): p. 113-120.
73. Shewach, D. S, and T. S. Lawrence, *Radiosensitization of human solid tumor cell lines with gemcitabine.* Seminars in Oncology, 1996. 23(5): p. 65-71.
74. Shewach, D. S., T. M. Hahn, et al., *Metabolism of 2',2'-Difluoro-2'-Deoxycytidine and radiation sensitization of human colon carcinoma cells.* Cancer Research, 1994. 54: p. 3218-3223.
75. Pegram, M. D., D. Baly, et al. *Antibody dependent cell-mediated cytotoxicity in breast cancer patients in Phase III clinical trials of a humanized anti-HER2 antibody [abstract].* Proc Am Assoc Cancer Res, 1997, 38: p. 602.
76. Heinemann, V., Y. Xu, et al., *Cellular elimination of 2',2'-Difluorodeoxycytidine 5'-Triphosphate: a mechanism of self-potentiation.* Cancer Research, 1992. 52: p. 533-539.

---

The invention claimed is:

1. A combination for use in the treatment of pancreatic cancer comprising:
   (i) an anti-gastrin effective immunogenic composition;
   (ii) an anti-CCKB/gastrin receptor peptide effective immunogenic composition, wherein the anti-CCKB/gastrin receptor peptide comprises SEQ ID NO: 1 or SEQ ID NO: 2; and
   (iii) one or more chemotherapeutic agents selected from the group consisting of a pharmaceutically active taxane, gemcitabine, and irinotecan.

2. The combination of claim 1, wherein the anti-gastrin effective immunogenic composition is selected from immunogens comprising an epitope of the gastrin peptide G17 covalently linked through a spacer peptide to an immunogenic protein or fragment thereof.

3. The combination of claim 1, wherein the anti-gastrin effective immunogenic composition comprises a conjugate of an aminoterminal G17 peptide epitope covalently linked to a seven amino acid residue peptide spacer which is attached to an ε-amino side chain of an immunogenic carrier protein lysine residue.

4. The combination of claim 1, wherein the anti-CCKB/gastrin receptor peptide effective immunogenic composition comprises a conjugate of SEQ ID NO: 1 attached to an ε-amino side chain of an immunogenic carrier protein lysine residue.

5. The combination of claim 4, wherein the amount of immunogen in the anti-gastrin effective immunogenic composition is about 250 μg to 500 μg per dose.

6. The combination of claim 1, wherein the anti-gastrin effective immunogenic composition is formulated in a water-in-oil emulsion suitable for intramuscular injection.

7. The combination of claim 1, wherein the amount of immunogen in the anti-gastrin effective immunogenic composition ranges from 10 μg to 5000 μg of the immunogen per dose.

8. The combination of claim 1, wherein the chemotherapeutic agent is gemcitabine.

9. The combination of claim 1, wherein the amount of immunogen in the anti-gastrin effective immunogenic composition is about 250 μg to 500 μg per dose.

10. The combination of claim 1, wherein the chemotherapeutic agent is irinotecan.

11. A combination for use in the treatment of pancreatic cancer comprising:
(i) an anti-gastrin effective immunological agent, wherein the anti-gastrin effective immunological agent is a monoclonal antibody or polyclonal antibodies derived from antisera produced in a patient by immunization with an anti-gastrin immunogenic composition;
(ii) an anti-gastrin receptor effective immunological agent, wherein the anti-gastrin receptor effective immunological agent is a monoclonal antibody or polyclonal antibodies derived from antisera produced in a patient by immunization with an anti-gastrin receptor immunogenic composition, and further wherein the anti-gastrin receptor immunogenic composition comprises an anti-CCKB/gastrin receptor peptide comprising SEQ ID NO: 1 or SEQ ID NO: 2; and
(iii) one or more chemotherapeutic agents selected from the group consisting of a pharmaceutically active taxane, gemcitabine, and irinotecan.

12. The combination of claim 11, wherein the chemotherapeutic agent is gemcitabine.

13. A method for treating pancreatic cancer in a patient, comprising administering to the patient a gastrin-immunoneutralizing immunogenic composition, wherein the immunogenic composition comprises an immunogen directed to eliciting neutralizing antibodies against a CCK-B/gastrin receptor peptide comprising SEQ ID NO: 1 or SEQ ID NO: 2; and administering to the patient a pharmaceutical composition of one or more chemotherapeutic agents selected from the group consisting of a pharmaceutically active taxane, gemcitabine, and irinotecan.

14. The method of claim 13, wherein the chemotherapeutic agent is gemcitabine.

15. The method of claim 13, wherein the patient has metastatic pancreatic cancer.

* * * * *